US009526506B2

(12) United States Patent
Shibata et al.

(10) Patent No.: US 9,526,506 B2
(45) Date of Patent: Dec. 27, 2016

(54) DEVICE FOR TREATING LUMEN OF LIVING BODY

(71) Applicant: TERUMO KABUSHIKI KAISHA, Shibuya-ku (JP)

(72) Inventors: Hideaki Shibata, Ashigarakami-gun (JP); Naoki Ishii, Ashigarakami-gun (JP); Satoshi Sawada, Ashigarakami-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 14/444,615

(22) Filed: Jul. 28, 2014

(65) Prior Publication Data

US 2015/0032087 A1    Jan. 29, 2015

Related U.S. Application Data

(60) Provisional application No. 61/859,507, filed on Jul. 29, 2013.

(30) Foreign Application Priority Data

Sep. 27, 2013 (JP) .................. 2013-202727
Sep. 27, 2013 (JP) .................. 2013-202729

(51) Int. Cl.
*A61M 31/00* (2006.01)
*A61B 17/12* (2006.01)
(Continued)

(52) U.S. Cl.
CPC ... *A61B 17/12186* (2013.01); *A61B 17/12036* (2013.01); *A61B 17/12045* (2013.01); *A61B 17/12136* (2013.01); *A61B 17/00491* (2013.01); *A61B 2017/00893* (2013.01); *A61B 2017/00938* (2013.01); *A61B 2217/005* (2013.01); *A61M 25/1002* (2013.01); *A61M 2025/105* (2013.01); *A61M 2025/1052* (2013.01)

(58) Field of Classification Search
CPC ................. A61B 17/12136; A61M 2025/105; A61M 25/1002
USPC ....................... 604/103.07, 103.02
See application file for complete search history.

(56) References Cited

U.S. PATENT DOCUMENTS 5,554,119 A    9/1996  Harrison et al.
5,665,063 A    9/1997  Roth et al.
(Continued)

FOREIGN PATENT DOCUMENTS

JP    04-261668 A    9/1992
JP    05-184681 A    7/1993
(Continued)

*Primary Examiner* — Kevin C Sirmons
*Assistant Examiner* — Deanna K Hall
(74) *Attorney, Agent, or Firm* — Buchanan Ingersoll & Rooney PC

(57) ABSTRACT

A device for treating the lumen of a living body includes a shaft insertable into a blood vessel, and a balloon provided on the shaft and shiftable between a deflated state and an expanded state. In the expanded state, the balloon has a recessed portion configured to form a coating chamber which is substantially blocked between an inner surface of the blood vessels and the device for treating the lumen of a living body, a discharge port provided on the recessed portion to discharge a coating substance toward the coating chamber; and a suction port provided on the recessed portion to apply a negative pressure to the coating chamber.

20 Claims, 17 Drawing Sheets

(51) Int. Cl.
*A61M 25/10* (2013.01)
*A61B 17/00* (2006.01)

(56) References Cited

U.S. PATENT DOCUMENTS

| | | | |
|---|---|---|---|
| 6,267,747 B1 * | 7/2001 | Samson | A61M 25/10 604/103.01 |
| 6,485,500 B1 | 11/2002 | Kokish et al. | |
| 9,119,943 B2 * | 9/2015 | Haery | A61M 25/09 |
| 2011/0077216 A1 | 3/2011 | Kastrup et al. | |
| 2011/0218517 A1 | 9/2011 | Ogle et al. | |

FOREIGN PATENT DOCUMENTS

| | | |
|---|---|---|
| JP | 10-502267 A | 3/1998 |
| JP | 11-319103 A | 11/1999 |
| JP | 2011-110144 A | 6/2011 |
| JP | 2014-014403 A | 1/2014 |
| WO | WO 2014/006738 A1 | 1/2014 |

\* cited by examiner

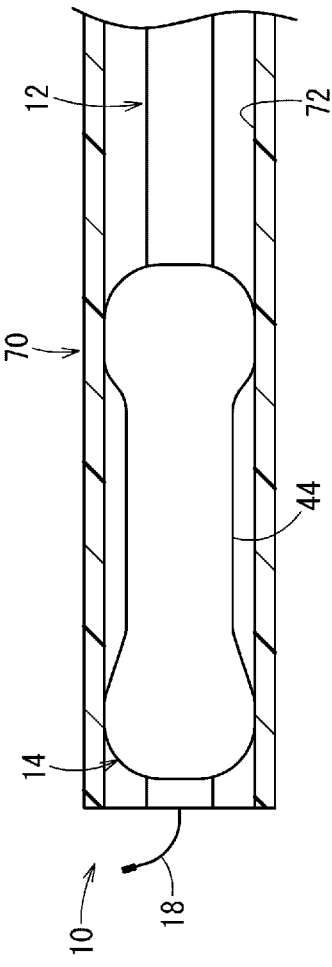
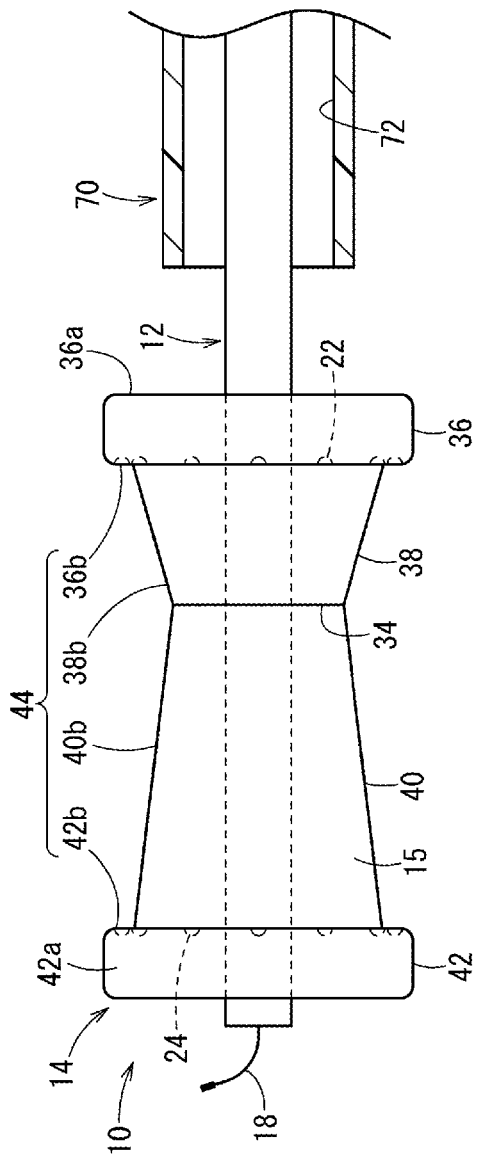

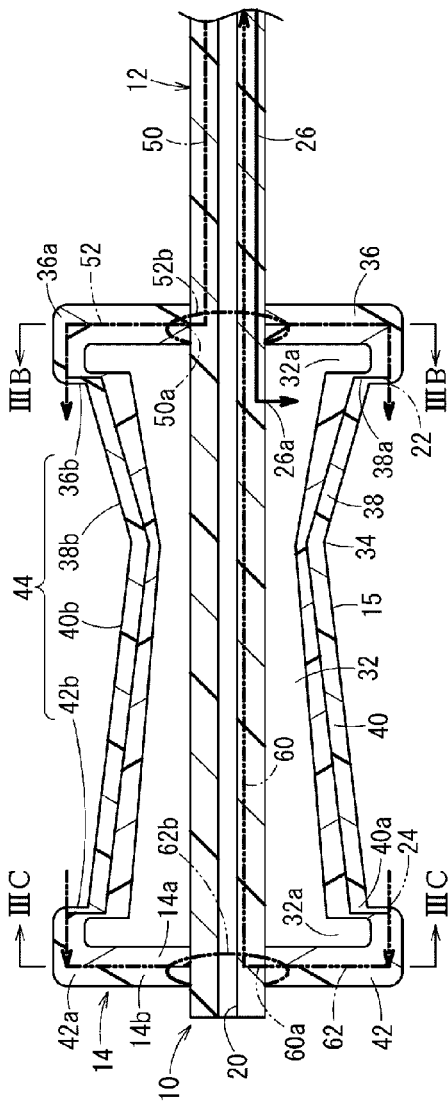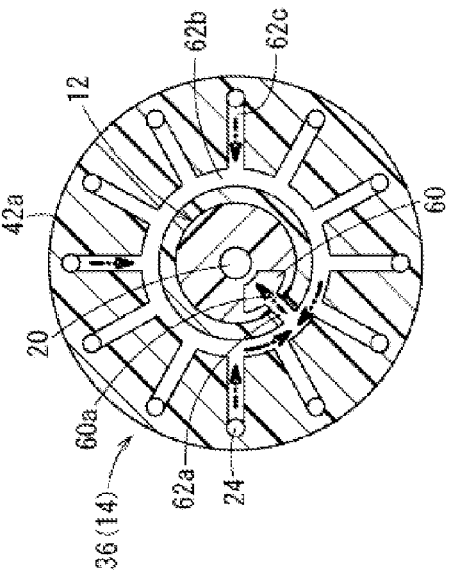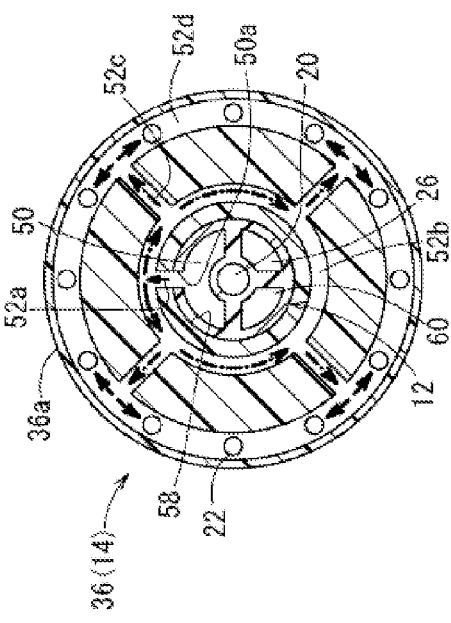

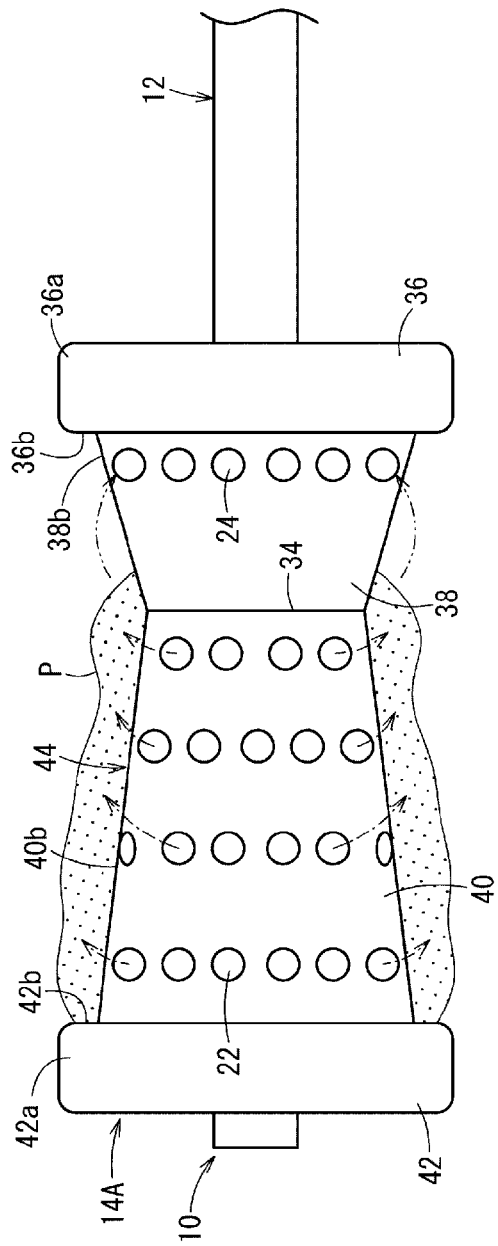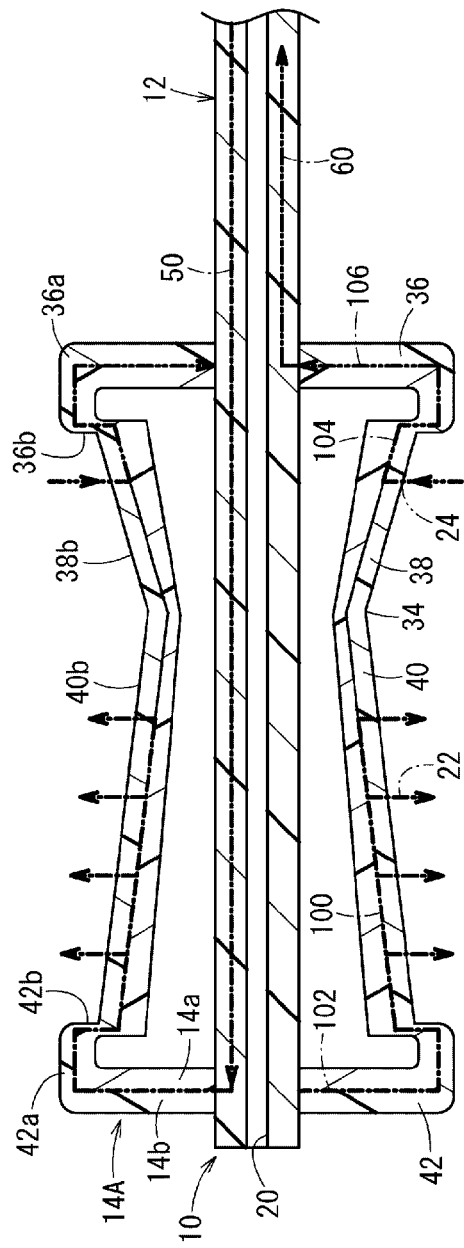

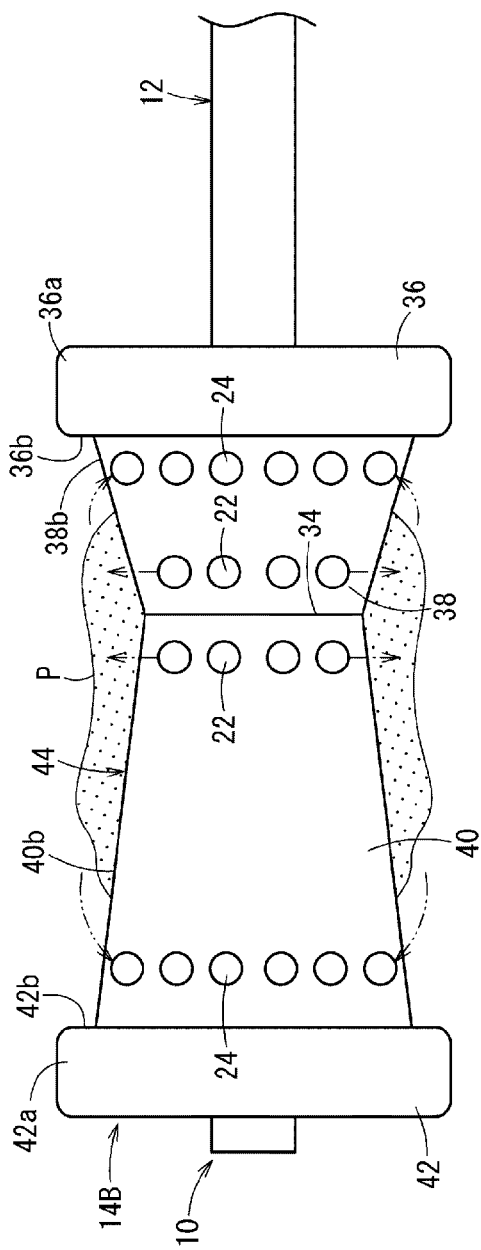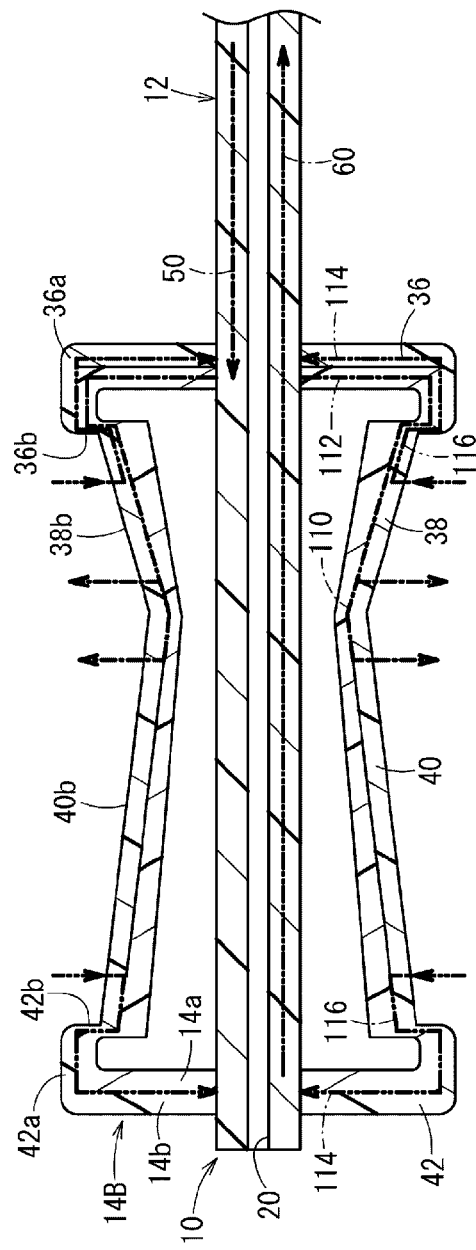

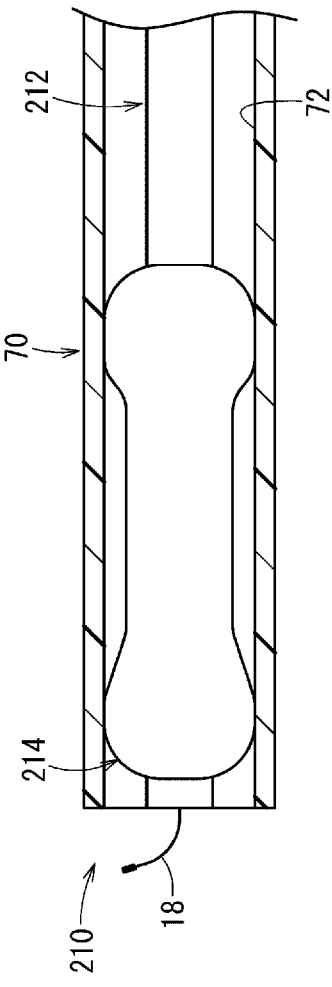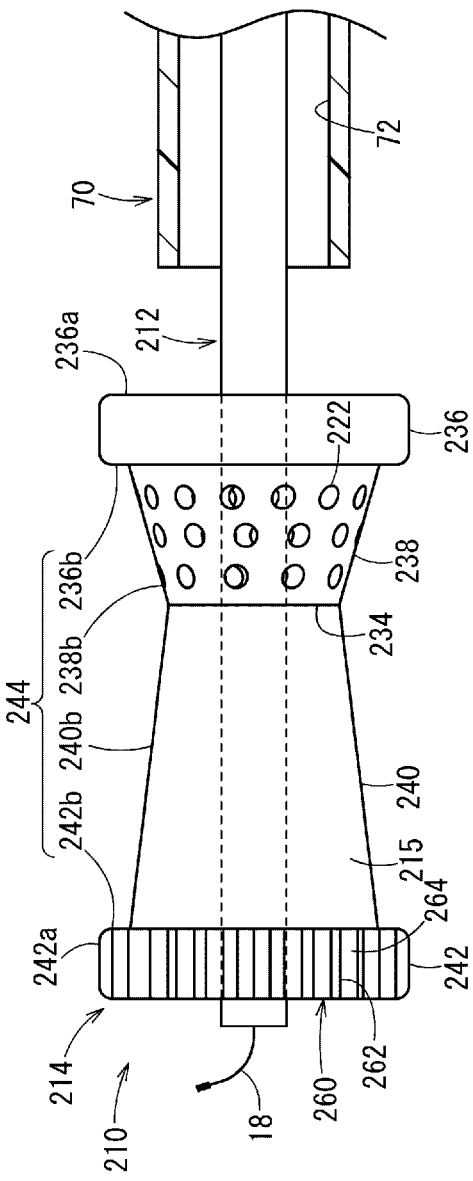

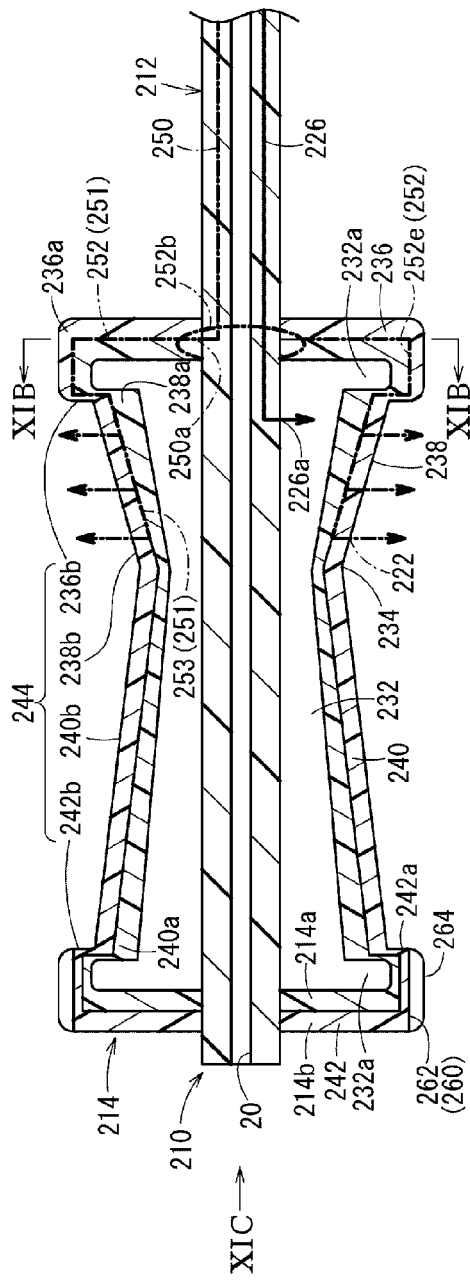
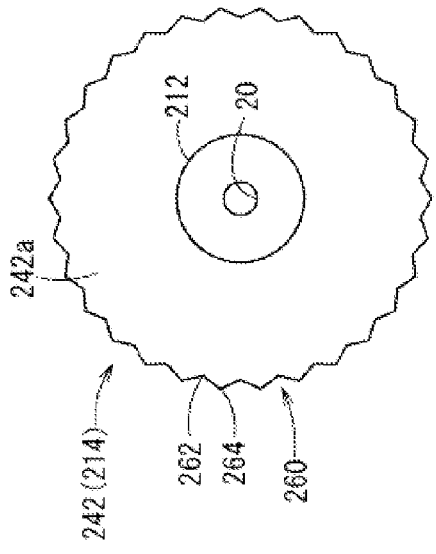
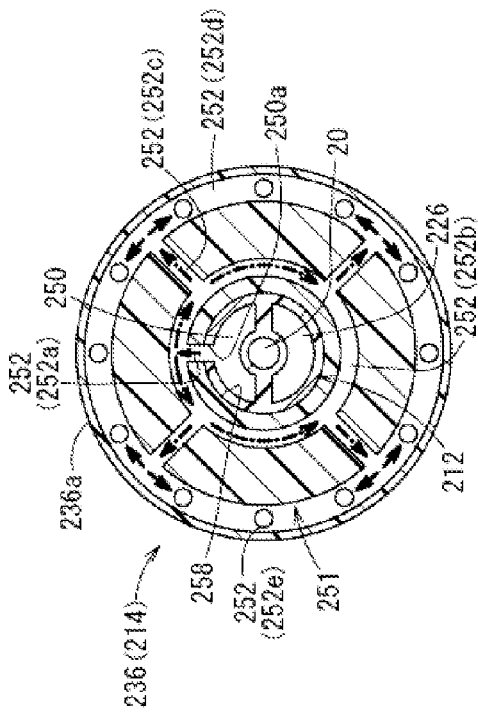

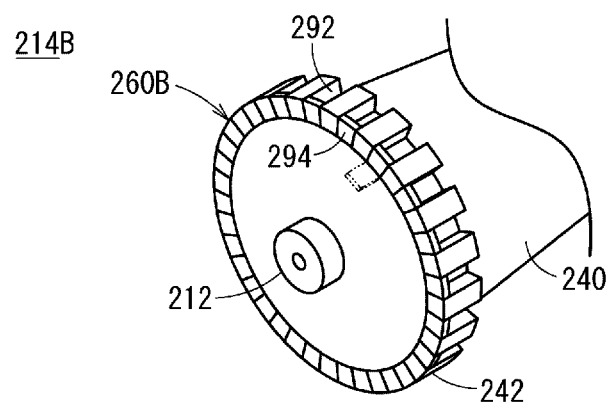
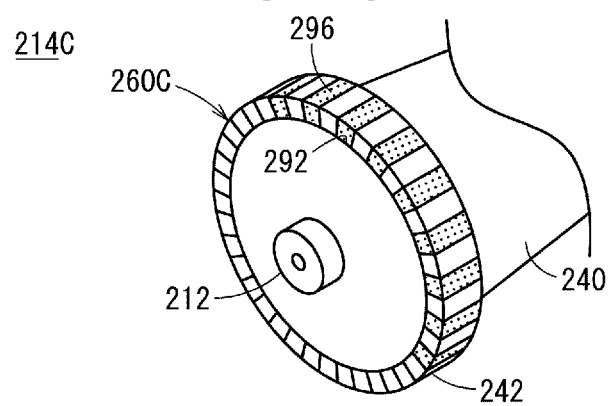
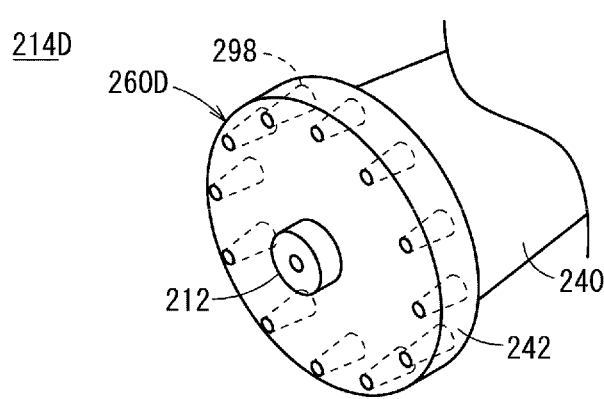

DEVICE FOR TREATING LUMEN OF LIVING BODY

CROSS REFERENCES TO RELATED APPLICATIONS

This application claims priority under 35 U.S.C. §119(e) to U.S. Application No. 61/859,507 filed on Jul. 29, 2013 and also claims priority under 35 U.S.C. §119(a) to Japanese Application No. 2013-202727 filed on Sep. 27, 2013 and Japanese Application No. 2013-202729 filed on Sep. 27, 2013, the entire content of all three of which is incorporated herein by reference.

TECHNICAL FIELD

The disclosure here generally relates to a device for treating a lumen of a living body. More specifically, the disclosure involves a device that treats a lumen of a living body by applying a coating substance onto the inside of the lumen of a living body.

BACKGROUND DISCUSSION

A procedure that delivers a treatment device through the inside of the lumen of a living body to provide predetermined treatment with respect to a lesion area occurring in biological organs (for example, the blood vessels, the bile ducts, the trachea, the esophagus, the urethra, the nasal cavity, or other organs) has been known. For example, while treating a narrowed area of the blood vessels, a delivery device for delivering a stent (including a drug-eluting stent (DES)) that enlarges the blood vessel wall from the inside thereof, a drug-eluting balloon catheter (DEB), or the like has been used. In addition, in recent years, treatment involving cutting (ablating) the nerve on the inside of the renal artery or the like has been conducted using an ablation device that can be delivered through the inside of the blood vessels as a treatment device, for example.

However, in the above-described procedure, it has been found that the elastic lamina in the intima cracks or fractures due to the treatment device coming into contact with or dilating (the intima of) the thickened blood vessel wall, or inflammation or damage is caused to the blood vessel wall accompanied by the contact of the treatment device. Furthermore, an adverse effect, in which a thrombus is formed inside the blood vessel and causes an embolism (embolus) in the peripheral blood vessel or restenosis is caused in the treated site, also occurs after the treatment.

For this reason, in recent years, a treatment method of coating a substance, such as alginate-catechol, which is gelated (i.e., becomes gelatinous) in a living body, and a coating substance thereof, which are disclosed in U.S. Patent Application Publication No. 2011/0077216 have been proposed. A catechol group is bonded to the blood vessel wall and the catechol groups are crosslinked with each other by adding an oxidant such as periodate to make the coating substance alkaline. Moreover, the alginate-catechol is gelated (becomes gelatinous) in a short period of time. As a result, it is possible to favorably coat the lumen of a living body such as the blood vessels, with the coating substance.

In addition, U.S. Patent Application Publication No. 2011/0077216 discloses a treatment device for coating the above-described coating substance. The device is a tubular shaped member (catheter) that can be delivered through the inside of the blood vessels. The treatment device is configured to have a discharge port on a side surface of a distal portion and to coat the blood vessel wall with the coating substance through the discharge port after the distal portion is delivered to a treatment subject inside the blood vessels by an operator.

However, in the treatment of coating the coating substance inside the blood vessels, when coating a coating substance having a low viscosity, the coating substance after being coated is swept away by the blood. For this reason, during the coating, it is preferable to coat a coating substance having a high viscosity. However, in this case, discharge resistance of the coating substance increases and it is difficult to precisely coat a desired area to be treated, with the coating substance by simply coating onto the inner surface of the blood vessels through the discharge port of the treatment device as disclosed in U.S. Patent Application Publication No. 2011/0077216.

In addition, the coating substance having a high viscosity is affected by flow of blood (blood flow) after being coated onto the blood vessels. As a result, there is a possibility that the shape of the coating layer is easily changed to an unintended shape, and thereby the ability of treating the treatment subject deteriorates. For example, it is considered that while the gelation reaction is completed after the coating, if the gelation completes in a state in which a distal section (outlet side of the blood flow) of the coating layer swells by shear stress due to the blood flow causing a step in the coating layer, the step promotes formation of a thrombus by causing disturbance of the blood flow or retention of blood, and as a result, the ability of the treatment rather deteriorates.

SUMMARY

The lumen treatment device here can favorably treat the lumen of a living body by applying a coating layer in a desired coating state to coat a treatment subject with a coating substance.

According to one aspect disclosed here, a device for treating a lumen of a living body comprises a shaft configured to be inserted into the lumen of the living body an expansion and deflation body provided on the shaft and changeable between a deflated state and an expanded state, and wherein, in the expanded state, the expansion and deflation body includes: at least one recessed portion configured to form a coating chamber which is substantially blocked between an inner surface of the lumen of the living body and the expansion and deflation body; a discharge port which is provided on the recessed portion and which discharges a coating substance toward the coating chamber; and a suction port which is provided on the recessed portion and which aspirates fluid from the coating chamber.

Here, the device effects substantial blocking, which refers to a sealed state to the extent that the coating substance discharged from the discharge port does not leak to the outside of the coating chamber by the viscosity of the coating substance in the coating chamber which is formed in the expanded state of the expansion and deflation body.

The device for treating the lumen of a living body can promote the flowing of the coating substance in the coating chamber which is substantially blocked, by discharging the coating substance toward the coating chamber from the discharge port and by further aspirating the fluid in the coating chamber through the suction port. For this reason, it is possible to form a coating layer which has a coating shape and is within a range for coating in accordance with the recessed portion by filling the inside of the coating chamber with the coating substance. Accordingly, it is possible to make the coating layer of the coating substance have an appropriate shape and to favorably treat the treatment subject in the lumen of a living body. In addition, the suction port can create an environment in which it is possible to favorably coat the coating substance by aspirating the fluid existing in the coating chamber before the coating of the coating substance. Furthermore, it is possible to simultaneously discharge the coating substance to the inside of the coating chamber and discharge the liquid in the coating chamber to the outside of the coating chamber by separately providing the discharge port and the suction port in the recessed portion of the expansion and deflation body. Thus, it is possible to adjust the pressure within the coating chamber. For this reason, it is possible to suppress the burden to the lumen wall of a living body and the outflow of the coating substance from the coating chamber, which are due to an increase in the pressure within the coating chamber.

In this case, the expansion and deflation body may be formed in a tubular shape in the expanded state, and possesses two end portions at opposite axial ends of the body, with one of the end portions of the body in the expanded state including an outwardly protruding first protruding portion, and the other end portion of the body in the expanded state including an outwardly protruding second protruding portion. The body in the expanded state also includes an intermediate portion possessing an outer surface, wherein the first and second protruding portions protruding outwardly beyond the outer surface of the intermediate portion of the body in the expanded state.

The expansion and deflation body has the first protruding portion and the second protruding portion, and as a result, it is possible to set the coating chamber that coats the coating substance to be in a relatively wide range of area between the first protruding portion and the second protruding portion. In this manner, it is possible to make the coating substance flow using the discharge port and the suction port even with such a wide coating chamber. Thus, it is possible to favorably coat the coating substance.

In addition, the discharge port may be formed on a facing surface of the second protruding portion that faces the first protruding portion, and the suction port may be formed on a facing surface of the first protruding portion that faces the second protruding portion.

The device for treating the lumen of a living body discharges the coating substance toward the inside of the coating chamber from the discharge port of the first protruding portion and aspirates the fluid from the suction port of the second protruding portion, thereby the coating substance can smoothly flow in the axial direction of the coating chamber. Accordingly, it is possible to simply fill the inside of the coating chamber with the coating substance.

The recessed portion may have a first inclination portion connected to the first protruding portion and a second inclination portion connected to the second protruding portion. It is preferable that a connection portion at which the first and second inclination portions are connected to each other is recessed most inward in the radial direction in the recessed portion.

The device for treating the lumen of a living body can coat the inner surface of the lumen of a living body with the coating substance using the first and the second inclination portions and the connection portion, as a chevron-like coating layer. Accordingly, it is possible to make the coating layer smooth and favorably cover the treatment subject caused by the influence of the flow of the body fluid after the coating. In addition, in a case where the range of the treatment subject is narrow, it is possible to perform the coating of the coating substance so as to match the chevron-like top portion to the treatment subject.

In the expanded state, the connection portion may be disposed at a position deviated further toward the first protruding portion than the center of the recessed portion in the axial direction of the recessed portion.

The device for treating the lumen of a living body can coat the coating substance such that the top portion of the coating layer is made to lean to the upstream side from which the body fluid flows, by providing the connection portion in the position leaning further on the first protruding portion side than the central portion of the expansion and deflation body in the axial direction, for example. Accordingly, an even coating layer is formed due to the influence of the body fluid flowing through the inside of the lumen of a living body.

Furthermore, a plurality of the discharge ports may be provided along a circumferential direction of the first inclination portion and a plurality of the suction ports may be provided along a circumferential direction of the second inclination portion.

The device for treating the lumen of a living body can evenly coat the inner surface of the lumen of a living body constituting the coating chamber with the coating substance by providing the discharge ports on the first inclination portion and the suction ports on the second inclination portion along the circumferential direction, respectively.

The plurality of discharge ports may also be arranged along the axial direction of the first inclination portion.

In this manner, when there are a plurality of discharge ports in the axial direction of the first inclination portion, it is possible to coat the coating chamber with a large quantity of the coating substance which can be made to flow to the second inclination portion side, thereby performing the treatment in a short period of time.

The plurality of discharge ports may be provided along the circumferential direction near the connection portion of the first and the second inclination portions, and the plurality of suction ports may be provided along the circumferential direction near the first protruding portion of the first inclination portion and along the circumferential direction near the second protruding portion of the second inclination portion.

The device for treating the lumen of a living body can facilitate flow of the coating substance so that the coating substance heads to both the end portions of the expansion and deflation body from the vicinity of the connection portion by providing the discharge ports and the suction ports in this manner. In this case, it is also possible to perform the treatment in a short period of time.

In addition, the expansion and deflation body can have a plurality of axially spaced coating portions, each possessing an inclination portion on a discharge port side to which the discharge port is provided connected to an inclination portion on a suction port side to which the suction port is provided, the inclination portion on the discharge port side being axially arranged relative to the inclination portion on the suction port side.

The device for treating the lumen of a living body can coat the coating substance so as to have a plurality of chevrons of the coating substance by providing a plurality of coating portions along the axial direction of the expansion and deflation body.

According to another aspect, a device for treating a lumen of a living body includes a shaft configured to be inserted into the lumen of the living body, and an expansion and deflation body provided on the shaft and changeable between a deflated state and an expanded state. In the expanded state, the expansion and deflation body includes: at least one axially extending recessed portion that includes a first inclination portion and a second inclination portion that are inclined in different directions and arranged axially adjacent one another to form a coating chamber between an inner surface of the lumen of the living body and the expansion and deflation body in the expanded state when the expansion and deflation body is positioned in the lumen and expanded to the expanded state; and a discharge port on the first inclination portion and on the second inclination portion which discharges a coating substance toward the coating chamber. In the expanded state, a connection portion of the recessed portion at which the first inclination portion and the second inclination portion are connected is disposed at a position axially deviated in a proximal end direction from a center of the recessed portion.

The device for treating the lumen of a living body can form a chevron shape, in which the top point is deviated, as a coating layer of the coating substance since the connection portion of the first and the second inclination portions is at a position deviated to the proximal side from the central portion in the axial direction of the recessed portion. For this reason, when the device is used within the blood vessels, it is possible to make the chevron-like coating layer smooth through the blood flow and to change the chevron-like coating layer so as to have an appropriate coating shape and to be within an appropriate range for coating after the coating, by coating the coating substance such that the top portion of the coating layer is deviated to the upstream side of blood flowing through the inside of the blood vessels. For example, in a case where the coating substance is a substance such as alginate-catechol requiring time up to the completion of the gelation reaction, it is important to form the shape of the coating layer by considering that the coating layer is swept away to the downstream side by the shear stress due to the body fluid, using the coating substance before the coating substance is gelated. For this reason, in a case of forming the coating layer within the lumen of a living body such as the blood vessels, the top portion which is more easily affected by the shear stress may be coated with the coating substance so as to be deviated to the upstream side of the body fluid (blood flow in a case of the blood vessels) flowing through the inside of the lumen of a living body by considering that the flow velocity of the body fluid becomes high following the central axis of the lumen of a living body. Accordingly, the shape of the coating layer with respect to the treatment subject in the lumen of a living body becomes more uniform, and therefore, it is possible to favorably perform the treatment.

In addition, with the provision of the discharge port on at least any one of the first inclination portion and the second inclination portion, it is possible to push blood remaining in the recessed portion or the substituted saline solution to both the ends of the recessed portion while the coating substance discharged to the coating chamber forms the coating layer toward the blood vessel wall. Accordingly, it is possible to more favorably form the coating layer which is filled with the coating substance.

Also, the expansion and deflation body may be formed in a tubular shape in the expanded state and both end portions in a longitudinal axial direction of the expansion and deflation body may include a first protruding portion and a second protruding portion which are abutted on or brought close to the inner surface of the lumen of a living body.

The expansion and deflation body has the first protruding portion and the second protruding portion at both end portions in the axial direction, and as a result, it is possible to set the coating chamber that coats the coating substance to be in a wide range of area between the first protruding portion and the second protruding portion. It is possible to fill the inside of the recessed portion with the coating substance by allowing the discharge port provided on the first and the second inclination portions to obliquely discharge the coating substance even with such a wide coating chamber.

Furthermore, the first protruding portion may be provided at a proximal portion of the expansion and deflation body and the first inclination portion may be connected to an end portion outwardly in a radial direction. The second protruding portion may be provided at a distal portion of the expansion and deflation body and the second inclination portion may be connected to an end portion outwardly in a radial direction.

The device for treating the lumen of a living body can favorably maintain the expanded state of the expansion and deflation body by allowing the first protruding portion provided at the proximal portion to support the first inclination portion and by allowing the second protruding portion provided at the distal side to support the second inclination portion. Using the configuration, the expansion and deflation body can form an annular shaped coating layer of the coating substance along the circumferential direction within the lumen of a living body.

The discharge port may be provided on the first inclination portion and the second protruding portion may have discharge openings capable of discharging a fluid within the coating chamber from the coating chamber.

The device for treating the lumen of a living body can discharge the fluid within the coating chamber through openings while discharging the coating substance toward the inside of the coating chamber from the discharge port by providing the openings. Accordingly, it is possible to discharge the coating substance without applying a strong pressure within the coating chamber. In addition, the coating substance discharged excessively toward the coating chamber from the discharge port may be discharged to the outside of the coating chamber through the openings. In this manner, the device for treating the lumen of a living body can control the flow of the coating substance within the coating chamber using the openings. For example, with the provision of the second protruding portion with the openings, it is possible to make the liquid in the coating chamber flow in the axial direction of the axis where the discharge port is connected to the openings and to guide the flow of the coating substance in the coating chamber to the lumen wall of the living body. Furthermore, the flow of the coating substance in the coating chamber is more easily controlled by providing the second protruding portion including the discharge openings on a surface opposite to the first inclination portion including the discharge port.

Furthermore, it is possible to use the difference in viscosity between the coating substance, and blood remaining in the coating chamber or the saline solution which is used while substituting the delivery flow path with the coating substance, by strictly controlling the flow of the fluid using the discharge openings. For example, the operator can also check whether the saline solution within the coating chamber is substituted with the coating substance by using the difference of the pressure during the coating in the injection portion on the hand side.

The discharge openings may be provided at the second protruding portion and be configured to have a communication path that communicates the coating chamber with the outside of the expansion and deflation body.

The device for treating the lumen of a living body can discharge the fluid in the coating chamber to the outside of the expansion and deflation body through the communication path. Therefore, it is unnecessary to provide a structure or the like for aspirating a substance as discharge openings, thereby making the configuration simple. For this reason, it is possible to not only simplify the actual procedure, but also to reduce the manufacturing cost.

Furthermore, the expansion and deflation body may be configured to have an inner balloon that has an inner space communicated with a lumen of the shaft for expansion fluid, and an outer balloon that covers the outside of the inner balloon. A flow path communicated with the discharge port may be provided between the inner balloon and the outer balloon.

It is possible to simply form the flow path guiding the coating substance to the discharge port by making the expansion and deflation body to have the double structure of the inner balloon and the outer balloon.

Furthermore, the shaft may have a lumen for discharging which communicates with the discharge port and means for reducing flow resistance that reduces the flow resistance of the coating substance may be provided on an inner surface constituting the lumen for discharging.

With the provision of means for reducing flow resistance in the lumen for discharging, the device for treating the lumen of a living body can reduce the discharge resistance during the discharging of the coating substance and smoothly guide the coating substance to the outside of the discharge port.

Furthermore, means for reducing adhesion of a coating substance that reduces adhesion of the coating substance may be provided on the surface of the expansion and deflation body. In specific, means for reducing adhesion of a coating substance is a process of providing the surface of the expansion and deflation body with hydrophobicity or a water-repellent property. Examples of such processes include coating, fine processing of the surface, or the like.

In the device for treating the lumen of a living body, in the process of providing the surface of the expansion and deflation body with the hydrophobicity or the water-repellent property, the adhesion of the coating substance onto the expansion and deflation body is suppressed even if the viscosity of the coating layer increases after the coating of the coating substance. For this reason, it is possible to favorably maintain the shape of the coating layer even while retrieving the expansion and deflation body.

According to another aspect, a method for treating a lumen of a living body, comprises: positioning an expansion and deflation body in the lumen of the living body, and outwardly expanding the expansion and deflation body while the expansion and deflation body is positioned in the lumen of the living body so that the expansion and deflation body is in an expanded state. The expansion and deflation body in the expanded state includes at least one recessed portion possessing an outer surface spaced from an inner surface of the lumen of the living body so that a space exists between the outer surface of the recessed portion and an inner surface of the lumen. The method further involves discharging a coating substance into the space between the outer surface of the recessed portion and an inner surface of the lumen while the expansion and deflation body is in the expanded state to form a coating layer of the coating substance on the inner surface of the lumen in the living body, and deflating the expansion and deflation body and removing the expansion and deflation body from the lumen of the living body while the coating layer of the coating substance remains on the inner surface of the lumen in the living body.

BRIEF DESCRIPTION OF DRAWINGS

FIG. 2A is a cross-sectional side view showing a deflated state of a balloon of FIG. 1, and FIG. 2B is a cross-sectional side view showing an expanded state of the balloon shown in FIG. 1.

FIG. 3A is a cross-sectional side view schematically showing a configuration of a distal portion of the treatment device of FIG. 1, FIG. 3B is a cross-sectional view taken along the section line IIIB-IIIB of FIG. 3A, and FIG. 3C is a cross-sectional view taken along the section line IIIC-IIIC of FIG. 3A.

FIG. 6A is a side view showing a distal portion of a treatment device according to a first modification example, and FIG. 6B is a cross-sectional side view schematically showing the configuration of the distal portion of the treatment device of FIG. 6A.

FIG. 7A is a side view showing a distal portion of a treatment device according to a second modification example. FIG. 7B is a cross-sectional side view schematically showing the configuration of the distal portion of the treatment device of FIG. 7A.

FIG. 10A is a cross-sectional side view showing a deflated state of a balloon of FIG. 9, and FIG. 10B is a cross-sectional side view showing an expanded state of the balloon shown in FIG. 9.

FIG. 11A is a cross-sectional side view schematically showing a configuration of a distal portion of the treatment device of FIG. 9, FIG. 11B is a cross-sectional view taken along the section line XIB-XIB of FIG. 11A, and FIG. 11C is a front view facing the treatment device of FIG. 11A from a distal side thereof.

FIG. 15A is an enlarged perspective view showing discharge means according to a fifth modification example, FIG. 15B is an enlarged perspective view showing discharge means according to a sixth modification example, and FIG. 15C is an enlarged perspective view showing discharge means according to a seventh modification example.

DETAILED DESCRIPTION

Figure 1:
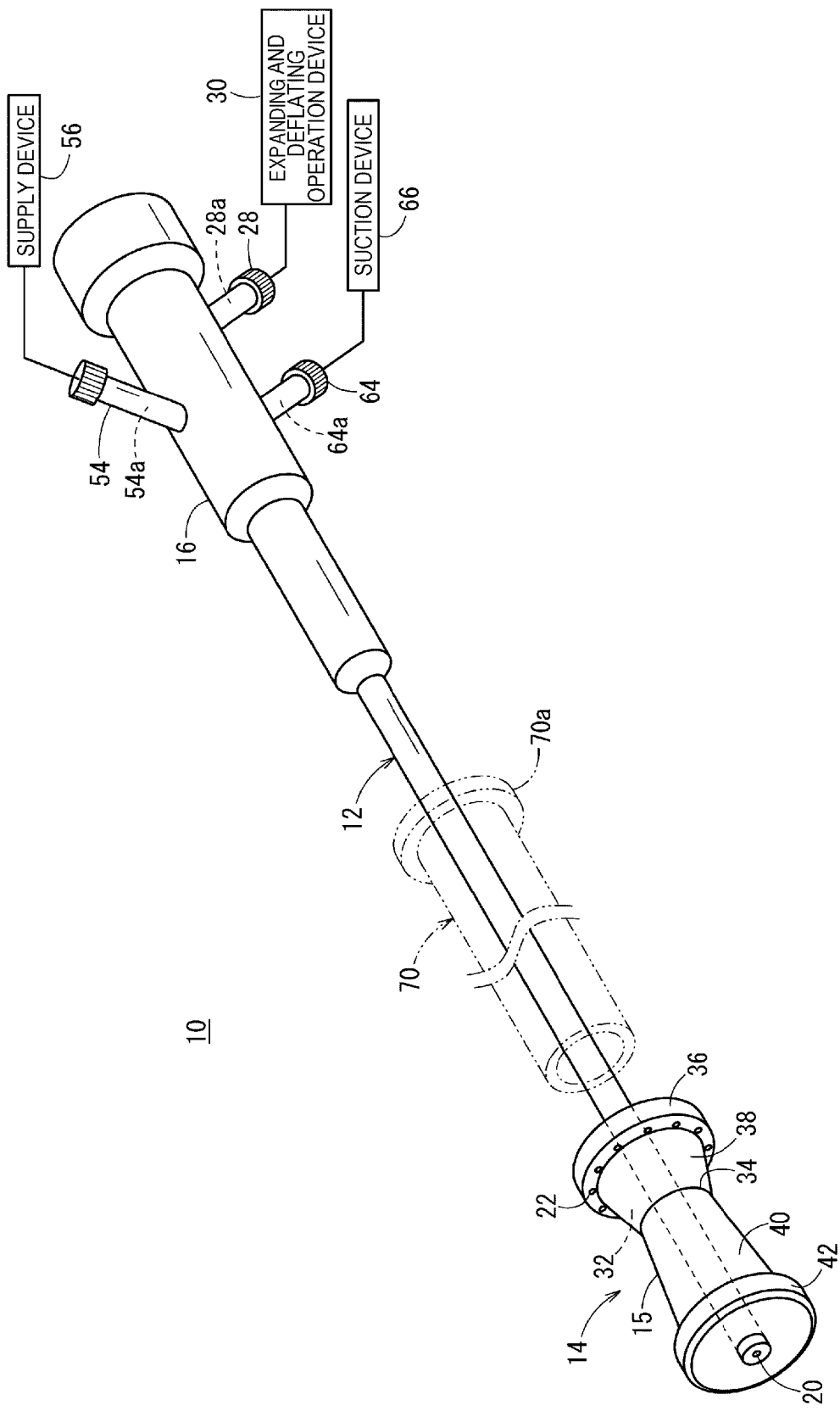
FIG. 1 is a perspective view showing an overall configuration of a device for treating the lumen of a living body according to a first embodiment of the present invention.

Hereinafter, a device for treating the lumen of a living body according to the disclosure here will be described in detail, referring to the drawing figures, with reference to various embodiments representing examples of the lumen treating device disclosed here.

A device 10 for treating the lumen of a living body (hereinafter, also simply referred to as treatment device 10) according to a first embodiment shown in FIG. 1 is a device which is used for coating lumens (blood vessels) of a living body with a coating substance. The operator performs an intervention procedure in which the treatment device 10 is inserted to the blood vessels through a small hole opened on the skin and is delivered to a treatment subject or site through the inside of the blood vessels to coat the treatment subject, with the coating substance. In particular, the treatment device 10 can be used in combination with treatment using other devices such as a balloon catheter, a stent delivery device, and the like. Moreover, the treatment device can also preferably coat the coating substance for treating the blood vessel wall (inner surface of the blood vessels) which has been treated with other devices.

For example, in balloon angioplasty, the periphery of a narrowed blood vessel is coated with the coating substance using the treatment device 10 after performing a procedure of dilating the narrowed blood vessel using the balloon catheter. In addition, in a stent implantation technique, the periphery of an implantation site of a stent is coated with the coating substance using the treatment device 10 after performing a procedure of implanting the stent in the narrowed blood vessel. Furthermore, in atherectomy, the periphery of a removal site is coated with the coating substance using the treatment device 10 after performing removal of atheroma (plaque) or calcified lesion which has accumulated on the blood vessel wall using an atherectomy device. Alternatively, in sympathetic nerve ablation treatment, the blood vessel wall in the periphery of a treated site is coated with the coating substance using the treatment device 10 after performing treatment of cutting the sympathetic nerve which passes through the inside of the blood vessel wall. Furthermore, as preventative treatment of the rupture of vulnerable plaque which is considered as a main cause of acute myocardial infarction, it is possible to prevent the rupture of plaque in advance by coating the plaque that has a possibility of rupture with the coating substance.

The treatment device 10 can be used for various applications and is not limited to the above-described the usage. In addition, as a matter of course, it is possible to apply the treatment device to various treatments of the inside of the lumen (for example, the bile ducts, the trachea, the esophagus, the urethra, the nasal cavity, other organs, or the like) of a living body.

The coating substance coated or applied to the treatment subject in the blood vessels has a function (including improvement or protection) of treating the blood vessels. An example includes alginate-catechol that exhibits a strong adhesion power with respect to the blood vessel wall. As described above, the alginate-catechol is gelated (i.e., becomes gelatinous) within the blood vessels in a relatively short period of time. For this reason, it is possible to protect inflammation or the like occurring at the treatment subject and to suppress the formation of restenosis or thrombus in the treatment subject. As a matter of course, the substance to be coated is not limited to the alginate-catechol. Examples thereof include polysaccharides such as heparin and hyaluronic acid, a betaine-based polymer, or a catechol modifier of polyethylene glycol. As a matter of course, various drugs that contain a biological substance which is physiologically active may be simultaneously applied in addition to the coating substance. For example, in a case where the coating substance is a substance such as alginate-catechol which is gelated within the blood vessels, it is possible to protect the blood vessel wall with gel and to release a drug to a treatment subject after gelation of the coating substance by mixing the drug or a drug-containing particle with the coating substance and by applying the mixture to the treatment subject.

In the following description, the treatment device 10 that coats a drug containing alginate-catechol will be representatively described in detail. In particular, the solution to be coated is in a state in which the viscosity increases over time by adjusting the pH of the substance to make the solution alkaline. In the following description, the coating substance while being coated in the blood vessels is called pre-gel solution. The pre-gel solution forms a gel-like coating layer by being gelated or becoming gelatinous (having a viscosity of an implantable degree) in a relatively short period of time after being coated to the blood vessels. That is, before applying or coating the coating solution to the blood vessel, the coating solution is mixed with alkaline solution so that the coating solution becomes alkaline. In some cases, the coating solution may mix with a crosslinking agent (for example, an oxidation agent) and alkaline solution. When the coating solution becomes alkaline, the viscosity of the coating solution increases over time. Thus, after the coating solution is applied to or coated on the blood vessel, the coating solution becomes more gelatinous as time passes and so the coating solution becomes the coating layer which does not flow with the blood. That is, the coating layer is able to withstand the blood flow.

As shown in FIG. 1, the treatment device 10 according to the first embodiment includes an elongated shaft 12 and a balloon 14 (expansion and deflation body) provided at the distal side or distal end of the shaft 12. The balloon 14 represents the coating portion of the treatment device 10 which coats a treatment subject in a blood vessel with a pre-gel solution. The shaft 12 has a function of guiding the pre-gel solution to the balloon 14.

The shaft 12 is configured as a tubular body that is insertable in the blood vessels and is formed to have a total length and a thickness (outer diameter) so that the balloon 14 can reach the treatment subject. The balloon 14 is firmly fixed to the distal side of the shaft 12 and the balloon 14 is configured to freely move back and forth within the blood vessels integrally with the shaft 12. In addition, the proximal portion of the shaft 12 is provided with a hub 16 which the operator grips. The hub 16 has a larger diameter than the shaft 12 for ease of operation.

The shaft 12 is delivered along a guide wire 18 (refer to FIG. 2A) which has been previously inserted in the blood vessels. For this reason, a guide wire lumen 20 is provided inside the shaft 12. The guide wire lumen 20 extends from the distal end of the shaft 12 to the proximal end of the hub 16 along the axial direction so that the guide wire lumen 20 extends throughout the axial extent of both the shaft 12 and the hub 16 and is open at the distal end of the shaft 122 as well as the proximal end of the hub 16. That is, the treatment device 10 is an over-the-wire type catheter in which the entire shaft 12 is guided by the guide wire 18. The treatment device 10 is not limited to the over-the-wire type catheter and may be configured of a rapid exchange type in which the guide wire 18 is guided outside the shaft 12 at an intermediate or midway position.

The balloon 14 is a tubular (bag-like) member having flexibility and elasticity. The balloon 14 is configured to freely shift between a deflated state in which the outer circumferential surface (recessed portion 44) is adjacent to (closer to) the shaft 12 as shown in FIG. 2A and an expanded state in which the outer circumferential surface (recessed portion 44) is separated away from (farther from) the shaft 12 as shown in FIG. 2B. In addition, a discharge port 22 that ejects the pre-gel solution and a suction port 24 that aspirates the fluid in the recessed portion 44 are provided at predetermined positions in the balloon 14. That is, the treatment device 10 functions to expand and deflate the balloon 14 in the blood vessel, to discharge the pre-gel solution, and to aspirate the fluid.

Accordingly, in the following description, for easily understanding the lumen treatment device disclosed here, the configuration of the treatment device 10 will be described for each of the functional attributes or characteristics of the balloon 14. The function of expanding and deflating the balloon 14 is realized using a first lumen 26 of the shaft 12, the balloon 14 itself, a first port 28 of the hub 16, and an expanding and deflating operation device 30 which is connected to the first port 28, as shown in FIGS. 1 and 3A to 3C.

The first lumen 26 of the shaft 12 supplies the balloon 14 with fluid for expansion and is configured as a lumen for expansion fluid to discharge the fluid for expansion from the balloon 14. The axial center portion of the shaft 12 includes a guide wire lumen 20. The shaft 12 also includes first to third lumens 26, 50, and 60 along the outer peripheral direction of the guide wire lumen 20. The first lumen 26 is fan-shaped in section and surrounds substantially one fourth of the portion outside of the guide wire lumen 20. For example, in FIG. 3B, the first lumen 26 is provided in a right obliquely downward direction of the guide wire lumen 20. The first lumen 26 extends along the axial direction of the shaft 12 and the proximal end of the first lumen 26 communicates with a flow path 28a which is formed inside the first port 28 within the hub 16.

The distal end of the first lumen 26 is bent or angled outwardly in a radial direction of the shaft 12 at a position axially overlapping with the balloon 14 (i.e., the distal end of the first lumen 26 axially overlaps with a portion of the balloon) and communicates with the internal space 32 of the balloon 14 through a side surface opening 26a of the shaft 12. Accordingly, the fluid for expansion is supplied to or discharged from the internal space 32 of the balloon 14 through the first lumen 26. It is preferable that the shaft 12 be provided with a plurality of side surface openings 26a. The balloon 14 dilates outwardly in the radial direction of the shaft 12 by the fluid for expansion which is supplied to the internal space 32 and becomes the shape as shown in FIGS. 2B and 3A to 3C in the expanded state.

More specifically, the balloon 14 has a tubular shape having a constricted portion (constricted portion 34) on the whole in that, in an expanded state, a conical shape which becomes narrower or smaller in the distal end direction from the proximal portion and a conical shape which becomes narrower or smaller in the proximal end direction from the distal portion join in an intermediate portion of the balloon. That is, the two conical portions are joined at a place offset from the middle. More specifically, the balloon 14 is configured so that in the dilated or expanded state, the balloon has, from the proximal end toward the distal end, a proximal end protruding portion 36 (first protruding portion), a proximal end inclination portion 38 (first inclination portion), a distal end inclination portion 40 (second inclination portion), and a distal end protruding portion 42 (second protruding portion).

An inner portion, in a radial direction, of the proximal end protruding portion 36 and the distal end protruding portion 42 constitute a fixing portion of the balloon 14 which is fixed to the outer circumferential surface of the shaft 12. A proximal end protruding end portion 36a and a distal end protruding end portion 42a which are protruded portions are provided outwardly in a radial direction of the proximal end protruding portion 36 and the distal end protruding portion 42. The side circumferential surfaces (Radially outwardly facing surfaces) of the proximal end protruding end portion 36a and the distal end protruding end portion 42a come into contact with the inner surface of the blood vessels by being protruded in a direction orthogonal to the axial direction of the shaft 12 in the expanded state.

The proximal end protruding end portion 36a and the distal end protruding end portion 42a may be adjacent to the inner surface of the blood vessels without coming into contact with the inner surface of the blood vessels. In addition, the protruding heights of the proximal end protruding portion 36 and the distal end protruding portion 42 are substantially the same as each other in the first embodiment, but the protruding heights may be different from each other. In this case, it is possible to efficiently block the inflow of blood by performing a procedure so that either the proximal end protruding portion 36 or the distal end protruding portion 42 having a higher (greater) protruding height is positioned at an upstream side of the blood flow. For example, the proximal end protruding portion 36 can have a protruding height so as to abut on the inner surface of the blood vessels and the distal end protruding portion 42 can have a lower (lesser) protruding height than that of the proximal end protruding portion 36. Then, it is possible to block the inflow of blood into the recessed portion 44 using the proximal end protruding portion 36 during a procedure and by performing the procedure so that the proximal end protruding portion 36 is positioned at an upstream side of the blood flow.

The proximal end inclination portion 38 has a proximal end connecting end portion 38a which is of a size smaller than the proximal end protruding portion 36 and is connected to the proximal end protruding end portion 36a. More specifically, the proximal end inclination portion 38 is directly connected to the distal end surface 36b (the axially facing outer surface of the first protruding portion 36 that faces toward the second protruding portion 42). Accordingly, the distal end surface 36b (facing surface) that faces the distal end direction exists between the side circumferential surface of the proximal end protruding end portion 36a and the proximal end connecting end portion 38a. The proximal end inclination portion 38 shows a tapered shape gradually becoming smaller in outer diameter from the proximal end connecting end portion 38a toward the distal end direction, and the distal end of the proximal end inclination portion is connected to the proximal end of the distal end inclination portion 40.

The distal end inclination portion 40 has a tapered shape gradually becoming larger in outer diameter from the distal end of the proximal end inclination portion 38 toward the distal end direction. That is, the connection portion of the proximal end inclination portion 38 and the distal end inclination portion 40 in the balloon 14 is the constricted portion 34. The distal end inclination portion 40 is configured such that the length of distal end inclination portion 40 along the axial direction of the balloon 14 is longer than the length of the proximal end inclination portion 38 in the axial direction of the balloon 14. Accordingly, the inclination angle of the distal end inclination portion 40 in the axial direction of the balloon 14 is gentler than that of the proximal end inclination portion 38.

The distal end inclination portion 40 has a distal end connecting end portion 40a which is of a size smaller than the distal end protruding portion 42 and is connected to the distal end protruding end portion 42a. More specifically, the distal end inclination portion 42 is directly connected to a proximal end surface 36b (the axially facing outer surface of the second protruding portion 42 that faces toward the first protruding portion 36). Accordingly, the proximal end surface 42b that faces the proximal end direction exists between the side circumferential surface of the distal end protruding end portion 42a and the distal end connecting end portion 40a.

In addition, the balloon 14 is configured to have a double structure having an inner balloon 14a and an outer balloon 14b. The balloon has a flow path for the pre-gel solution or a flow path for applying a negative pressure between the inner balloon 14a and the outer balloon 14b. The inner balloon 14a has an internal space 32 therein and exhibits a shape formed of the above-described proximal end protruding portion 36, proximal end inclination portion 38, distal end inclination portion 40, and distal end protruding portion 42 when the fluid for expansion is supplied to the internal space 32. The internal space 32 is provided with a gap 32a between the proximal end protruding portion 36 and the proximal end inclination portion 38 and between the distal end inclination portion 40 and the distal end protruding portion 42, to thereby ease the folding of the balloon 14 in the deflated state. The outer balloon 14b deforms following the expansion of the inner balloon 14a by covering the inner balloon 14a.

The balloon 14 (outer balloon 14b) is dilated so as to have the recessed portion 44 which is configured to have the distal end surface 36b of the proximal end protruding portion 36, the outer circumferential surface 38b of the proximal end inclination portion 38, the outer circumferential surface 40b of the distal end inclination portion 40, and the proximal end surface 42b of the distal end protruding portion 42. In the expanded state, the balloon 14 forms a coating chamber X (refer to, for example, FIG. 4A) between the recessed portion 44 and the inner surface of the blood vessels by bringing the proximal end protruding portion 36 and the distal end protruding portion 42 into contact with the inner surface of the blood vessels.

The material constituting the balloon 14 is not particularly limited. Examples of the materials include natural rubber such as latex; resin materials such as synthetic rubber such as silicone rubber, urethane rubber, ethylene-propylene-diene rubber, nitrile rubber, fluoro rubber, and acrylic rubber; fibrous porous films such as woven fabrics, knits, non-woven fabrics, and paper materials; non-fibrous porous films; and dense films such as polymer sheets.

In addition, it is preferable that the outer surface of the balloon 14 (recessed portion 44) be provided with means for reducing adhesion of a coating substance which shows hydrophobicity or a water-repellent property. Examples of treatment methods include coating or fine processing of the surface. Among these, it is preferable that a coating film 15 that reduces the adhesion of the pre-gel solution be provided. An example of forming the coating film includes a coating agent having a water-repellent property or the like.

The fluid for expansion which is supplied to or discharged from the internal space 32 of the balloon 14 is not also particularly limited. For example, it is possible to preferably use a saline solution, an X-ray impermeable contrast agent, or the like. In particular, the contrast agent is effective because it is possible to confirm the expanded state of the balloon 14 under X-ray photography.

Returning to FIG. 1, the supply and the discharge of the fluid for expansion are operated by the expanding and deflating operation device 30 connected to the first port 28. The expanding and deflating operation device 30 is configured to have an indeflator, for example. The indeflator is a syringe-like device having a pressure meter and a plunger movable positioned in a barrel. The indeflator pushes out (supplies) the fluid for expansion while adjusting a pressurizing force during a pressing operation of a plunger (not shown) and aspirates (discharges) the fluid for expansion while adjusting a decompression force during a pulling operation of the plunger.

Next, a function of discharging the pre-gel solution will be described with reference to FIGS. 1 and 3A to 3C. The function of discharging the pre-gel solution is realized using a second lumen 50 of the shaft 12, a discharge guide path 52 and a discharge port 22 of the balloon 14, a second port 54 of the hub 16, and a supply device 56 which is connected to the second port 54. For more easily understanding the drawing, in FIG. 3A, the first lumen 26, the second lumen 50, the third lumen 60, the discharge guide path 52, a suction guide path 62, and communication ports 50a and 60a are illustrated with simple lines showing the route of fluid. More specifically, the route of the fluid for expansion is shown by a solid line, the flow path of the pre-gel solution is shown by a one-dot chain line, and the route for aspirating the fluid is shown by a two-dot chain line. In addition, FIG. 3A is illustrated with a perspective view in order to be more easily understood in that an inner path 52b of the discharge guide path 52 and an inner path 62b of the suction guide path 62 have an annular shape.

The second lumen 50 of the shaft 12 is a flow path (lumen for discharging) for supplying the pre-gel solution to the balloon 14. The second lumen 50 fan-shaped in cross-section and surrounds substantially one-half of the portion outside of the guide wire lumen 20. For example, in FIG. 3B, the second lumen 50 is provided so as to surround the upper half portion of the guide wire lumen 20. The second lumen 50 extends along the axial direction of the shaft 12 and the proximal side of the second lumen communicates with a flow path 54a which is formed inside of the second port 54 within the hub 16.

It is preferable that the size of the cross section of the flow path of the second lumen 50 be set or configured in accordance with the viscosity of the coating substance. For example, in a case where the coating substance is a pre-gel solution having a relatively high viscosity, the cross section of the flow path may be sufficiently larger (in the first embodiment, twice or more) than the cross section of the flow path of the first lumen 26 or the third lumen 60. Accordingly, it is possible to discharge the pre-gel solution by reducing the discharge resistance of the pre-gel solution significantly. In addition, it is preferable that super-water-repellent coating film 58 or a riblet structure be formed inside of the second lumen 50 as means for reducing flow resistance in order to reduce flow resistance (discharge resistance) of a pre-gel solution having a high viscosity. Here, the riblet structure refers to a structure having an effect of reducing the flow velocity resistance by providing a fine groove structure.

The distal end of the second lumen 50 is bent or angled outwardly in a radial direction of the shaft 12 at a position axially overlapping with the proximal end protruding portion 36 of the balloon 14 and communicates with the communication ports 50a connected to the discharge guide path 52 which is formed in the proximal end protruding portion 36.

The discharge guide path 52 is formed of a space provided between the inner balloon 14a and the outer balloon 14b. The space may be formed by providing a groove which is manufactured on the outer circumferential surface of the inner balloon 14a or the inner surface of the outer balloon 14b, or a tube. The discharge guide path 52 has a function of guiding the pre-gel solution outwardly in a radial direction from the communication ports 50a of the inside thereof. For example, the discharge guide path 52 includes an introduction path 52a which communicates with the communication ports 50a, an inner path 52b for circulating at a position close to the shaft 12, a plurality of intermediate paths 52c extending outwardly in a radial direction from the inner path 52b, and an outer path 52d which communicates with the intermediate paths 52c and circulates from a position close to the blood vessels.

The outer path 52d communicates with the discharge port 22. A plurality of discharge ports 22 are formed (12 ports in FIG. 3B) along a circumferential direction in the distal end surface 36b of the proximal end protruding portion 36. The discharge ports 22 are provided at even intervals from each other and the pre-gel solution guided to the outer path 52d is discharged to the coating chamber X. The outer path 52d extends also in a thickness direction of the proximal end protruding end portion 36a which is formed to be thick in the proximal end protruding portion 36 and comparatively strongly discharges the pre-gel solution which is discharged from the discharge ports 22 in the distal end direction (coating chamber X) from the distal end surface 36b.

Returning to FIG. 1, the supply of the pre-gel solution is operated using the supply device 56 which is connected to the second port 54. The supply device 56 has a storage tank which is formed of a reservoir and can store a sufficient amount of the pre-gel solution, for example. The storage tank is connected so as to be communicated with the flow path 54a of the second port 54. The reservoir has a function as a syringe that outputs the pre-gel solution by controlling the supply amount thereof, by being operated by an operator or the like. Accordingly, the pre-gel solution is supplied to the second port 54 from the reservoir at a desired timing and is then supplied to the second lumen 50.

Next, the function of applying (aspirating) a negative pressure will be described with reference to FIGS. 1 and 3A to 3C. The function of applying the negative pressure of the treatment device 10 is realized using the third lumen 60 of the shaft 12, the suction guide path 62 and the suction port 24 of the balloon 14, a third port 64 of the hub 16, and a suction device 66 which is connected to the third port 64.

The third lumen 60 of the shaft 12 is configured to have a flow path (lumen for discharging) for applying the negative pressure. The third lumen 60 is formed at a position and in a shape laterally symmetrical to the first lumen 26 as shown in FIG. 3B. The third lumen 60 extends along the axial direction of the shaft 12 and the proximal end of the third lumen 60 communicates with a flow path 64a which is formed inside the third port 64 in the hub 16.

The distal end of the third lumen 60 is bent or angled outwardly in a radial direction of the shaft 12 at a position axially overlapping with the distal end protruding portion 42 through the inside of the balloon 14 and communicates with the communication ports 60a connected to the suction guide path 62 which is formed in the distal end protruding portion 42. The suction guide path 62 is formed of a space provided between the inner balloon 14a and the outer balloon 14b similar to the discharge guide path 52. The space may be formed by providing a groove which is manufactured on the outer circumferential surface of the inner balloon 14a or the inner surface of the outer balloon 14b, or a tube. The suction guide path 62 communicate with the suction port 24 and has a function of guiding the substance existing in the coating chamber X inward in a radial direction through the suction port 24. The suction guide path 62 is formed of a material harder than that of the balloon 14 so as not to be blocked due to the negative pressure during the aspirating. For example, in a case where the suction guide path 62 is a groove formed inside the balloon, any material of the inner balloon 14a and the outer balloon 14b is formed of a material harder than that of the other balloon. Accordingly, the suction guide path 62 is not blocked even in a state in which the balloon 14 dilates and the distal end protruding portion 42 is pressed to the blood vessel wall. In particular, the expansion of the inner balloon 14a outwardly in a radial direction may be suppressed, that is, a material which is not dilated to more than some extent may be applied. In this manner, a balloon 14, which is formed of an outer balloon 14b made of a soft material, and an inner balloon 14a, which is provided with a groove being the suction guide path 62 and is formed of a hard (harder) material, is made, and it is relatively easy to maintain the suction guide path 62 even when the balloon 14 is pressurized. Thereby it is possible to suppress the blockage of the suction guide path 62.

For example, as shown in FIG. 3C, the suction guide path 62 includes a derivation path 62a which communicates with the communication ports 60a, an inner path 62b that circulates from a position close to the shaft 12, and a radial path 62c that faces the suction port 24 extending outwardly in a radial direction from the inner path 62b. The radial path 62c outwardly in a radial direction communicates with the suction port 24 by extending evenly in the thickness direction of the distal end protruding end portion 42a. A plurality of suction ports 24 are provided (12 ports in FIG. 3C) along the circumferential direction of the proximal end surface 42b of the distal end protruding portion 42. In this manner, in a case where the suction guide path 62 radially extends outwardly in a radial direction with respect to the axial line of the shaft 12, it is relatively easy to fold the balloon 14 even if the suction guide path 62 is formed of a material harder than that of the balloon 14, and to dilate and deflate the balloon 14, which is preferable.

The treatment device 10 aspirates the substance (blood, a saline solution, a pre-gel solution, or the like) existing in the coating chamber X from the plurality of suction ports 24 by applying the negative pressure from the third lumen 60. The substance aspirated from the suction ports 24 is guided to the third lumen 60 through the radial path 62c, the inner path 62b and the derivation path 62a and moves in the proximal end direction through the third lumen 60.

Returning to FIG. 1, the proximal side of the third lumen 60 is connected to the suction device 66 through the flow path 64a of the third port 64. The suction device 66 is formed of, for example, a vacuum pump and can apply the negative pressure, which is set by an operator, to the third lumen 60 at a desired timing.

The treatment device 10 according to the first embodiment is basically configured as described above. Next, the effect of the treatment device 10 will be described with reference to FIGS. 4A to 5C.

As an example, the treatment device 10 is used for coating a treated site (treatment subject A) of a blood vessel 80 with a pre-gel solution P after treating the blood vessel 80 using another device. In the following description, an example of using the treatment device 10 after atherectomy using an atherectomy device (not shown) will be representatively described.

The operator first identifies the form of a lesion area using angiography or intravascular ultrasonic diagnostics in the procedure. Next, the guide wire 18 is percutaneously introduced to the inside of the blood vessel 80 through the femur or the like using a seldinger technique and the atherectomy device is progressed along the guide wire 18, for example. Then, the blood vessel 80 is made to have an inner diameter with which blood can sufficiently flow in the inner surface 80a of the treatment subject (site) A, by removing (for example, scraping, pulverizing, or aspirating) the accumulated atheroma using the atherectomy device. After the treatment, the atherectomy is finished by removing the atherectomy device from the inside of the blood vessel 80.

Next, the treatment device 10 is inserted to the inside of the blood vessel 80 to coat the treatment subject A, from which the atheroma is removed, with the pre-gel solution P in consideration of the possibility of any damage occurring in the inner surface 80a of the blood vessel 80 by the atherectomy.

In this case, a delivery step of delivering the distal portion of the treatment device 10 to the treatment subject A is carried out. In the delivery step, the treatment device 10 is inserted through a site which is the same as the site through which the atherectomy device is inserted. During the delivery within the blood vessel 80, the treatment device 10 is guided along the guide wire 18 which is previously inserted, and therefore, it is possible to smoothly deliver the balloon 14 to the treatment subject A. Once the operator determines that the balloon 14 is overlapped with the treatment subject A, under radiographic visualization, the operator stops the delivery.

Figure 4A:
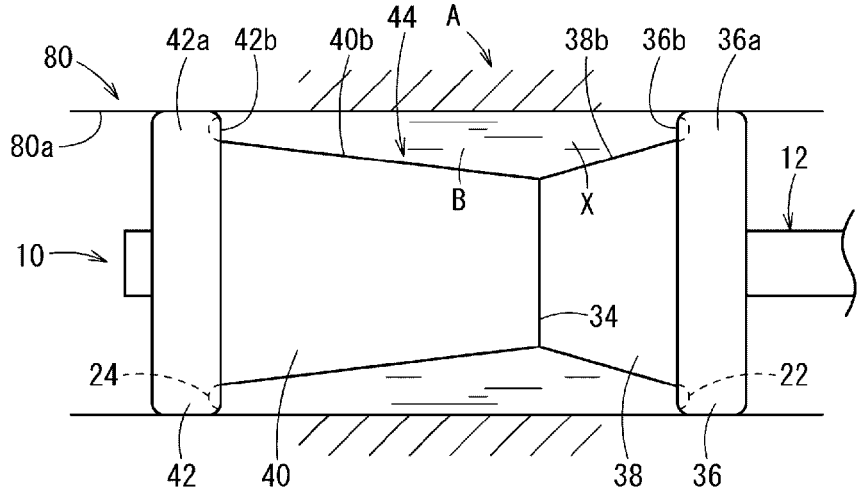
FIG. 4A is a first explanatory view describing a method of using the treatment device of FIG. 1.

After the delivery step, as shown in FIG. 4A, an expansion step of expanding the balloon 14 is carried out. In the expansion step, the fluid for expansion is supplied to the internal space 32 of the balloon 14 through the flow path 28a of the first port 28 and the first lumen 26 by operating the expanding and deflating operation device 30. Accordingly, the proximal end protruding portion 36 and the distal end protruding portion 42 of the balloon 14 come into contact with the inner surface 80a of the blood vessel 80, the blood flow is blocked, and the coating chamber X is formed, by which the blood flow is blocked by the recessed portion 44 and the inner surface 80a of the blood vessel 80, in the blocked space. For example, the balloon 14 may be configured to be folded in the delivery step and to be dilated by releasing the folding in the expansion step. Accordingly, it is possible to deliver the balloon 14 to the treatment subject A in a state of the balloon having a small outer diameter.

The blood B that flows through the inside of the blood vessel 80 is left within the coating chamber X. For this reason, a step of forming a coating environment which makes the coating environment of the pre-gel solution P be in a more favorable state is carried out before the coating of the pre-gel solution P.

Figure 4B:
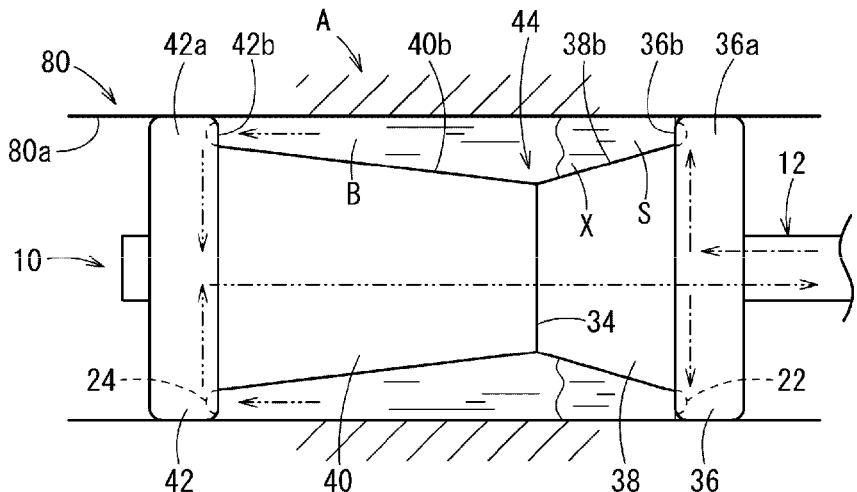
FIG. 4B is a second explanatory view describing the method of using the same subsequent to FIG. 4A.

In specific, a saline solution S is discharged from the discharge port 22 of the balloon 14. The saline solution S flows into the discharge guide path 52 of the balloon 14 through the flow path 54a of the second port 54 and the second lumen 50 of the shaft 12 using the supply device 56, flows into the discharge guide path 52 of the balloon 14, flows through the discharge guide path 52, and is discharged to the inside of the coating chamber X from the discharge port 22. As shown in FIG. 4B, the saline solution S which is discharged to the coating chamber X flows into the distal end by sweeping away the blood B existing in the coating chamber X.

Then, blood remaining in the coating chamber X is aspirated by operating the suction device 66 simultaneously with the operation of the supply device 56. That is, the suction port 24 applies a suction force using the suction device 66 with respect to the coating chamber X. In this manner, the blood B is aspirated from the suction port 24, sequentially flows through the radial path 62c, the inner path 62b, and the derivation path 62a of the suction guide path 62 of the balloon 14, and flows into the third lumen 60 of the shaft 12. Furthermore, the blood B moves in the proximal end direction of the third lumen 60 and is aspirated to the suction device 66 through the flow path 64a of the third port 64.

Figure 4C:
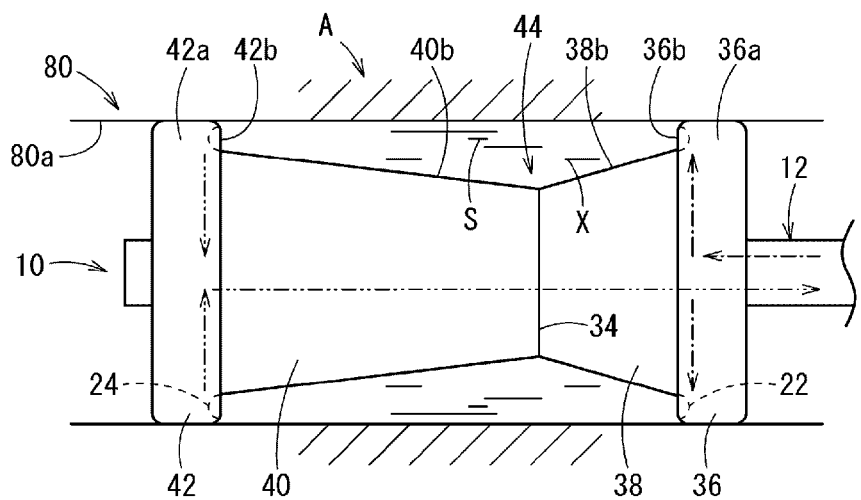
FIG. 4C is a third explanatory view describing the method of using the same subsequent to FIG. 4B.

Accordingly, the coating environment in which the coating chamber X is filled with the saline solution S is formed as shown in FIG. 4C. The pre-gel solution P hardly causes a chemical reaction with respect to the saline solution S, and therefore, the inside of the coating chamber X is favorably coated with the pre-gel solution in this environment. In addition, the treatment device 10 simultaneously performs the discharging of the saline solution S from the discharge port 22 and the aspirating of the blood B in the suction port 24. Thus, it is possible to form the coating environment without significantly changing the pressure exerted on the inside of the blocked coating chamber X. The step of forming a coating environment may not be carried out depending on the treatment situation.

After the inside of the coating chamber X is filled with the saline solution S, the pre-gel solution P is discharged to the inside of the coating chamber X (coating step). In addition, the operation of aspirating the saline solution S within the coating chamber X is also performed simultaneously with the discharging of the pre-gel solution P. Accordingly, it is possible to develop the pre-gel solution P in the coating chamber X while suppressing the significant increase of the inner pressure of the coating chamber X.

The pre-gel solution P moves through the flow path 54a of the second port 54 and the inside of the second lumen 50 of the shaft 12 in the distal end direction after being supplied from the supply device 56. At this time, super-water-repellent coating film 58 is formed on the inner surface of the second lumen 50, and therefore, the pre-gel solution P can smoothly flow through the inside of the second lumen 50.

Figure 5A:
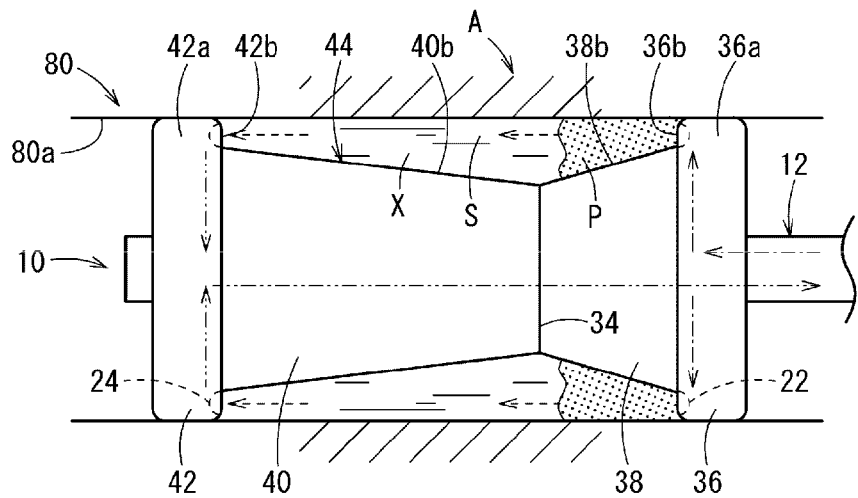
FIG. 5A is a fourth explanatory view describing the method of using the same subsequent to FIG. 4C.

Then, the pre-gel solution P flows into the discharge guide path 52 of the balloon 14 from the communication ports 50a of the second lumen 50. After the pre-gel solution P flows into the introduction path 52a, the pre-gel solution is diffused in the circumferential direction by passing through the inner path 52b and flows into the plurality of the intermediate paths 52c. Furthermore, the diffusion is promoted by the pre-gel solution flowing into the outer path 52d from the intermediate paths 52c. As shown in FIG. 5A, the pre-gel solution P which is guided to the outer path 52d is evenly discharged from the plurality of discharge ports 22 and flows through the outer circumferential surface of the balloon 14 so as to cover the outer circumferential surface of the balloon from the proximal side of the coating chamber X.

Figure 5B:
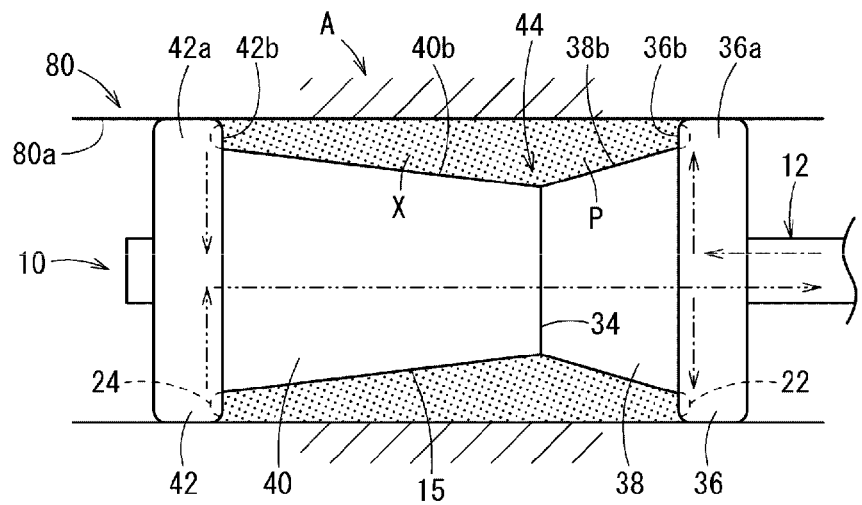
FIG. 5B is a fifth explanatory view describing the method of using the same subsequent to FIG. 5A.

In addition, the suction port 24 aspirates the saline solution S. Therefore, the saline solution S and the pre-gel solution P within the coating chamber X smoothly flow in the distal end direction in accordance with the discharging force from the discharge port 22 and the aspirating force of the suction port 24. As a result, as shown in FIG. 5B, the coating chamber X relatively easily enters a state of being filled with the pre-gel solution P from a state of being filled with the saline solution S. Once the inside of the coating chamber X is filled with the pre-gel solution P, the operations of the supply device 56 and the suction device 66 stop so as to stop the discharging operation and the aspirating operation. The discharging of the pre-gel solution P is preferably performed until the suction port 24 aspirates the pre-gel solution P to some extent. Accordingly, the coating chamber X is reliably filled with the pre-gel solution P.

The adhering of the pre-gel solution P to the blood vessel wall is actively promoted through the reaction between the catecol group and the blood vessel wall without being affected by the blood flow. In addition, the gelation reaction of the pre-gel solution P starts from the point in time of being adjusted to an alkaline solution. As a result, a gel-like coating layer C, the viscosity of which is further higher than viscosity during discharging, is formed on the inner surface 80a of the blood vessel 80 along the shape of the recessed portion 44 of the balloon 14.

After coating the pre-gel solution P, an operation of deflating the balloon 14, that is, an operation in which the expanding and deflating operation device 30 applies negative pressure to the balloon 14 is performed. Accordingly, the fluid for expansion is discharged from the internal space 32 of the balloon 14 through the first lumen 26 and the flow path 28a. The balloon 14 enters a deflated state accompanied by the outflow of the fluid for expansion.

Figure 5C:
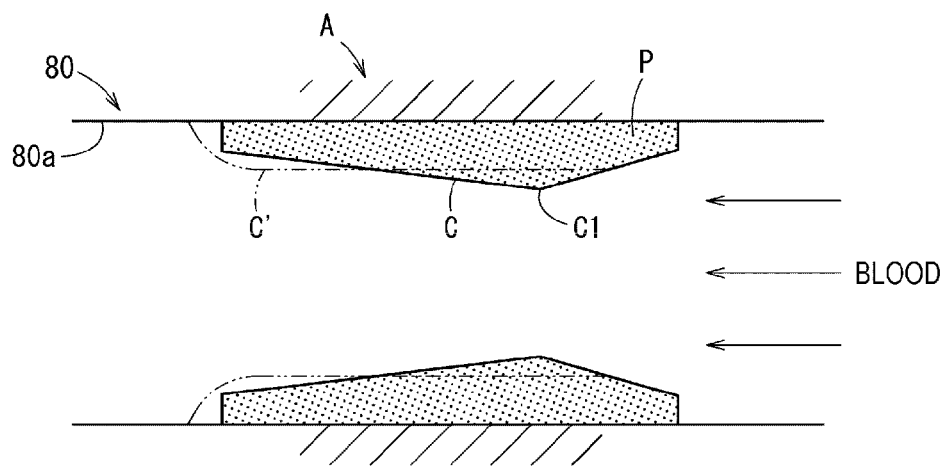
FIG. 5C is a sixth explanatory view describing the method of using the same subsequent to FIG. 5B.

After the deflating of the balloon 14, an operation of removing the treatment device 10 from the blood vessel 80 is performed. Accordingly, the gel-like coating layer C is implanted in the blood vessel 80 in a chevron cross section shape as shown in FIG. 5C. Here, the adhesion of the pre-gel solution P to the balloon 14 is suppressed by providing the coating film 15 on the surface of the balloon 14 even if the viscosity of the coating layer C increases after the coating of the pre-gel solution P. For this reason, it is possible to favorably maintain the shape of the coating layer C even while retrieving the treatment device 10.

In the coating layer C right after removing the treatment device 10, a top portion C1 of the chevron leans in the upstream direction of the blood flow based on the shape of the balloon 14. For this reason, once blood restarts flowing through the inside of the blood vessel 80 after the deflating of the treatment device 10, the area around the top portion C1 of the chevron of the coating layer C moves in the downstream direction by being affected by the flow of blood. That is, the coating layer C is changed to the coating layer C' which has an appropriate coating shape and is within an appropriate range for coating so as to be made smooth as shown by the two-dot chain line in FIG. 5C by the shear stress of the blood flow, thereby covering the treatment subject A. Accordingly, it is possible to favorably treat the treatment subject A. For example, in a case where the treatment subject A is relatively small in size, it is possible to treat the treatment subject A by placing the treatment subject A on the vicinity of the top portion C1 of the chevron of the coating layer C even if the coating layer C flows away by the shear stress of the blood flow. At this time, in the recessed portion 44 of the treatment device 10, it is preferable to provide the constricted portion 34 corresponding to the top portion C1 of the chevron of the coating layer C, with a contrast marker so as to ease the adjustment of the positions of the treatment device 10 and the treatment subject A.

As described above, in the treatment device 10 according to the first embodiment, when entering the expanded state of the balloon 14, it is possible to form the coating chamber X, which is substantially blocked, between the inner surface 80a of the blood vessel 80 in which the treatment subject A is located, and the recessed portion 44 of the balloon 14. Moreover, the suction port 24 provided on the recessed portion 44 can aspirate the substance located in the coating chamber X. Therefore, the coating chamber X creates an environment in which it is possible to favorably coat the pre-gel solution P. For this reason, the device 10 for treating the lumen of a living body can smoothly discharge the pre-gel solution P toward the coating chamber X from the discharge port 22. In addition, while discharging the pre-gel solution P, it is possible to promote the flow of the pre-gel solution P by applying the negative pressure to the coating chamber X from the suction port 24. Therefore, it is possible to accurately coat the inner surface 80a of the blood vessel 80 with the pre-gel solution P. Accordingly, the coated pre-gel solution P can favorably treat the treatment subject A in the blood vessels.

In this case, the balloon 14 has the proximal end protruding portion 36 and the distal end protruding portion 42, and therefore, it is possible to set the coating chamber X that coats the pre-gel solution P to be in a wide range of area between the proximal end protruding portion 36 and the distal end protruding portion 42. In this manner, it is possible to make the pre-gel solution P having a high viscosity flow using the discharge port 22 and the suction port 24 even with such a wide coating chamber X. Thus, it is possible to favorably coat the pre-gel solution P.

In addition, the treatment device 10 can make the pre-gel solution P smoothly flow along the distal end direction of the coating chamber X from the discharge port 22 by respectively providing the proximal end protruding portion 36 and the distal end protruding portion 42 with the discharge port 22. Accordingly, it is possible to simply fill the coating chamber X with the pre-gel solution P. Moreover, it is possible to reduce the discharge resistance of the pre-gel solution P by providing the proximal side, which is close to the supply side of the pre-gel solution P, with the discharge port 22. In the treatment device 10, the formation positions of the discharge port 22 and the suction port 24 may be reversed, that is, the proximal end protruding portion 36 may be provided with the suction port 24 and the distal end protruding portion 42 may be provided with the discharge port 22.

Furthermore, the treatment device 10 can coat the pre-gel solution P in a chevron shape with respect to the inner surface 80a of the blood vessel 80 by providing the proximal end inclination portion 38, the distal end inclination portion 40, and the constricted portion 34. In this case, the treatment device 10 can coat the pre-gel solution P such that the top portion C1 of the coating layer C is configured to lean to the upstream side from which blood flows, by providing the constricted portion 34 in the position leaning further on the proximal end protruding portion 36 side than the central portion of the balloon 14 in the axial direction. Accordingly, the pre-gel solution P comes to have a favorable coating shape at the time of the completion of the gelation reaction by being smoothed by blood flowing through the inside of the blood vessel 80.

Furthermore, it is possible to reduce (increase fluidity) the discharge resistance of the pre-gel solution P by providing the second lumen 50, through which the pre-gel solution P flows, with the super-water-repellent coating film 58. Accordingly, even the pre-gel solution having a high viscosity can be made to flow relatively easily. The super-water-repellent coating film 58 may be provided in the discharge guide path 52 or the flow path 54a. In addition, means for reducing flow resistance is not limited to the super-water-repellent coating film 58. For example, the fluidity of the pre-gel solution P may be increased by providing a fine riblet structure within the second lumen 50.

In addition, it is preferable that the treatment device 10 be configured so that the balloon 14 has a relatively small outer diameter in the delivery step of delivering the balloon 14 to the treatment subject A. As an example of such a configuration, folding the balloon 14 so as to be expandable is considered, but the treatment device is not limited to this example as long as the outer diameter of the balloon 14 is deflated so as to be expandable.

For example, as shown in FIGS. 1 and 2A, the balloon 14 may be protected during the delivery of the shaft 12 and the outer diameter of the balloon 14 may be deflated so as to be expandable by providing a sheath 70. The sheath 70 is formed of a tubular body having a smaller outer diameter than the inner diameter of the blood vessels to which the shaft is delivered. An accommodation lumen 72 that can accommodate the shaft 12 and the balloon 14 is formed in the sheath by penetration. The balloon 14 is accommodated in the vicinity of the opening of the distal end of the accommodation lumen 72.

The proximal portion of the sheath 70 is made to be exposed to the outside of a living body in a state in which the balloon 14 is delivered to the treatment subject A. Moreover, an operation plate 70a (sheath operating portion) of which the outer diameter is enlarged outwardly in a radial direction is formed in the proximal portion of the sheath. The sheath 70 makes the balloon 14 in the deflated state become exposed to the inside of the blood vessel 80 by operating the operation plate 70a and by causing the shaft 12 and the balloon 14 to relatively perform a reciprocating movement. It is possible to make the outer diameter of the balloon 14 small during the delivery of the balloon 14 with such a configuration.

The treatment device 10 is not limited to the above-described configuration and various modifications or application examples can be made. Hereinafter, several other modification examples of the treatment device 10 will be described. In the description of these other embodiments representing additional examples of the lumen treating device disclosed here, components that are the same as those of the treatment device 10 according to the first embodiment or configurations having the same function are identified by common reference numerals and a detailed description of such aspects is not repeated in the following description.

A balloon 14A according to a first modification example shown in FIGS. 6A and 6B is configured such that the distal end inclination portion 40 is provided with the discharge port 22 and the proximal end inclination portion 38 is provided with the suction port 24. Specifically, a plurality of discharge ports 22 are provided in the circumferential direction of the distal end inclination portion 40 and a plurality of rows of the discharge ports 22 (4 rows in FIG. 6A) are provided along the axial direction of the balloon 14A. The discharge ports 22 are configured so as to substantially evenly discharge the pre-gel solution P. The outer circumferential surface 40b of the distal end inclination portion 40 is inclined so as to slightly face the proximal side. Therefore, the pre-gel solution P (containing a saline solution S; the same applies hereinafter) which is discharged from the plurality of discharge ports 22 is encouraged to move in the proximal end direction.

For this reason, a plurality of discharge guide paths 100 on an inclination portion side extending in the proximal end direction are provided inside the distal end inclination portion 40 of the balloon 14A in accordance with the number of discharge ports 22 formed in the circumferential direction, and communicate with the discharge ports 22 arranged in the axial direction. The discharge guide paths 100 on an inclination portion side communicate with a discharge guide path 102 on a protruding portion side provided in the distal end protruding portion 42 of the balloon 14A and the pre-gel solution P can be substantially evenly supplied from the discharge guide path 102 on a protruding portion side. The discharge guide path 102 on a protruding portion side can be configured to be the same as the discharge guide path 52 of the treatment device 10 and communicates with the second lumen 50 extending to the distal end protruding portion 42 inside of the shaft 12 of the treatment device 10.

A plurality of suction ports 24 are provided in the circumferential direction at a position (proximal side) close to the proximal end protruding portion 36 of the proximal end inclination portion 38. Accordingly, the pre-gel solution P discharged from the discharge ports 22 rather easily flows to the proximal side of the coating chamber X. In addition, the proximal end inclination portion 38 is inclined so that the outer circumferential surface 38b slightly faces the distal side. Therefore, the suction ports 24 can apply the negative pressure to the distal side of the coating chamber X.

A plurality of suction guide paths 104 on an inclination portion side which are communicated with the suction ports 24 are provided inside the proximal end inclination portion 38. The suction guide paths 104 on an inclination portion side communicate with a suction guide path 106 on a protruding portion side which is provided inside the proximal end protruding portion 36. The suction guide path 106 on a protruding portion side can be configured to be the same as the suction guide path 62 of the treatment device 10 and communicates with the third lumen 60 extending to the proximal end protruding portion 36 inside the shaft 12 of the treatment device 10.

The balloon 14A according to the first modification example can favorably coat the coating chamber X, which is formed between the distal end protruding portion 42 and the proximal end protruding portion 36, with the pre-gel solution P. That is, the plurality of discharge ports 22 provided at the distal end inclination portion 40 can discharge the pre-gel solution P at a low discharge resistance. For this reason, the distal side of the coating chamber X is promptly filled with the pre-gel solution P. In addition, the plurality of suction ports 24 can aspirate the pre-gel solution P (or blood or saline solution S) discharged from the discharge ports 22 by applying the negative pressure in the distal end direction. Accordingly, the inside of the coating chamber X is promptly filled with the pre-gel solution P, and thereby it is possible to shorten the time required for the treatment. In addition, the pre-gel solution P is easily spread in the coating chamber X by providing the discharge ports 22 in the distal end inclination portion 40 having an inclination angle smaller than that of the proximal end inclination portion 38. As a matter of course, the formation positions the discharge ports 22 and the suction ports 24 may be reversed.

A balloon 14B according to a second modification example shown in FIGS. 7A and 7B includes the discharge ports 22 in the distal side of the proximal end inclination portion 38 and the proximal side of the distal end inclination portion 40, and includes the suction ports 24 in the proximal side of the proximal end inclination portion 38 and the distal side of the distal end inclination portion 40. For this reason, in the balloon 14B, a discharge guide path 110 on an inclination portion side is provided between the proximal end inclination portion 38 and the distal end inclination portion 40 and a discharge guide path 112 on a protruding portion side is provided in the proximal end protruding portion 36. In addition, a pair of suction guide paths 114 on a protruding portion side is provided in the proximal end protruding portion 36 and the distal end protruding portion 42. Moreover, a suction guide path 116 on an inclination portion side connected to the suction guide path 114 on a protruding portion side is provided which is short in the proximal end inclination portion 38 and the distal end inclination portion 40.

Accordingly, the balloon 14B discharges the pre-gel solution P toward the coating chamber X from the periphery (discharge port 22) of the constricted portion 34 after forming the coating chamber X between the blood vessel 80 and the balloon by expanding the balloon 14B. The pre-gel solution P is discharged from the plurality of discharge ports 22, and therefore, the discharge resistance is reduced. The pre-gel solution P discharged to the substantially central portion of the coating chamber X in the axial direction flows in the distal end direction and in the proximal end direction from the central portion. At this time, the suction port 24 applies the negative pressure to the distal side and the proximal side of the coating chamber X and aspirates the pre-gel solution P such that the pre-gel solution P faces both the end portions of the coating chamber X. For this reason, it is possible to smoothly fill the inside of the coating chamber X with the pre-gel solution P.

Accordingly, with the balloon 14B according to the second modification example, the coating chamber X is also promptly filled with the pre-gel solution P, and thereby it is possible to shorten the time required for the treatment. In addition, it is possible to previously coat the pre-gel solution P in a large quantity with respect to the thickest portion (top portion of the chevron) in the axial direction of the coating chamber X by providing the discharge port 22 in the vicinity of the constricted portion 34 of the balloon 14B.

In short, the formation positions, the number of formations, the shape or the like of the discharge ports 22 and the suction ports 24 formed in the balloons 14, 14A, and 14B are not particularly limited and can be freely set. In addition, the flow path of the discharge guide path 110 on an inclination portion side, the discharge guide path 112 on a protruding portion side, the suction guide path 114 on a protruding portion side, and the suction guide path 116 on an inclination portion side can also be freely set according to the formation positions of the discharge port 22 and the suction port 24.

Figure 8A:
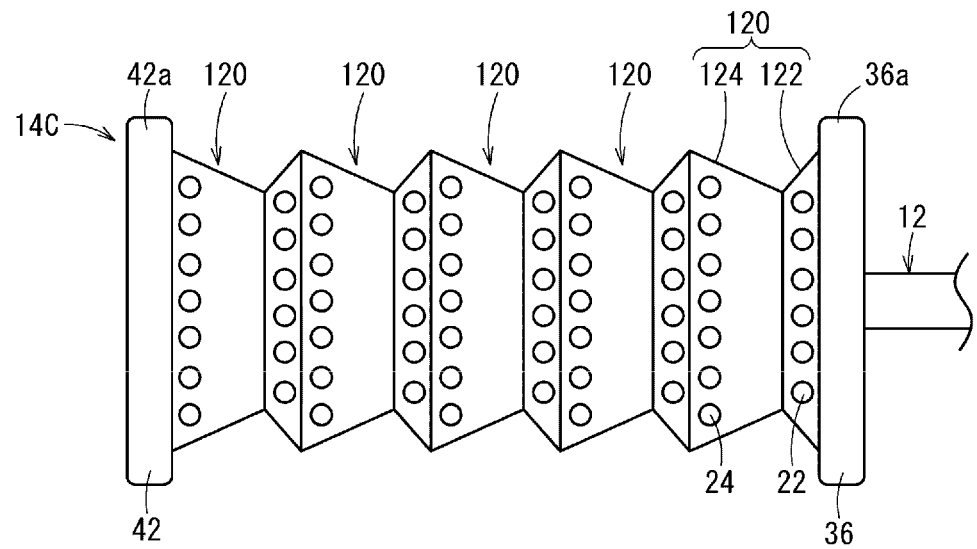
FIG. 8A is a side view showing a distal portion of a treatment device according to a third modification example.
Figure 8B:
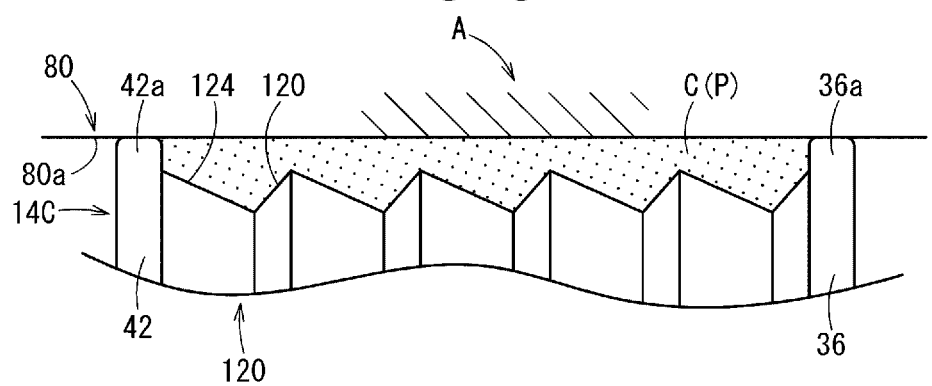
FIG. 8B is a partial side view showing a coating state of a coating substance of the treatment device of FIG. 8A.
Figure 8C:
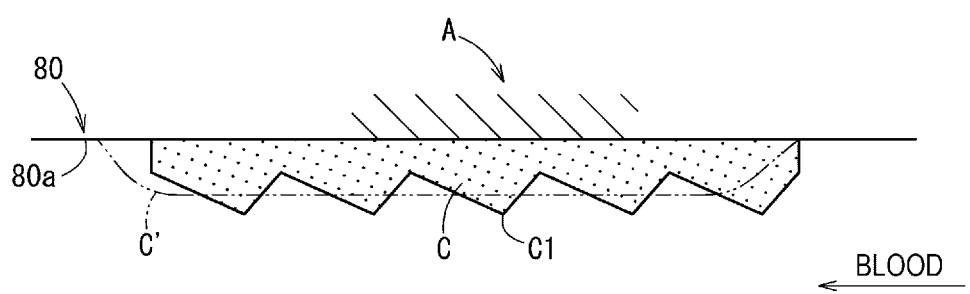
FIG. 8C is a partial side view showing a state of the coating substance after being coated subsequent to FIG. 8B.
Figure 9:
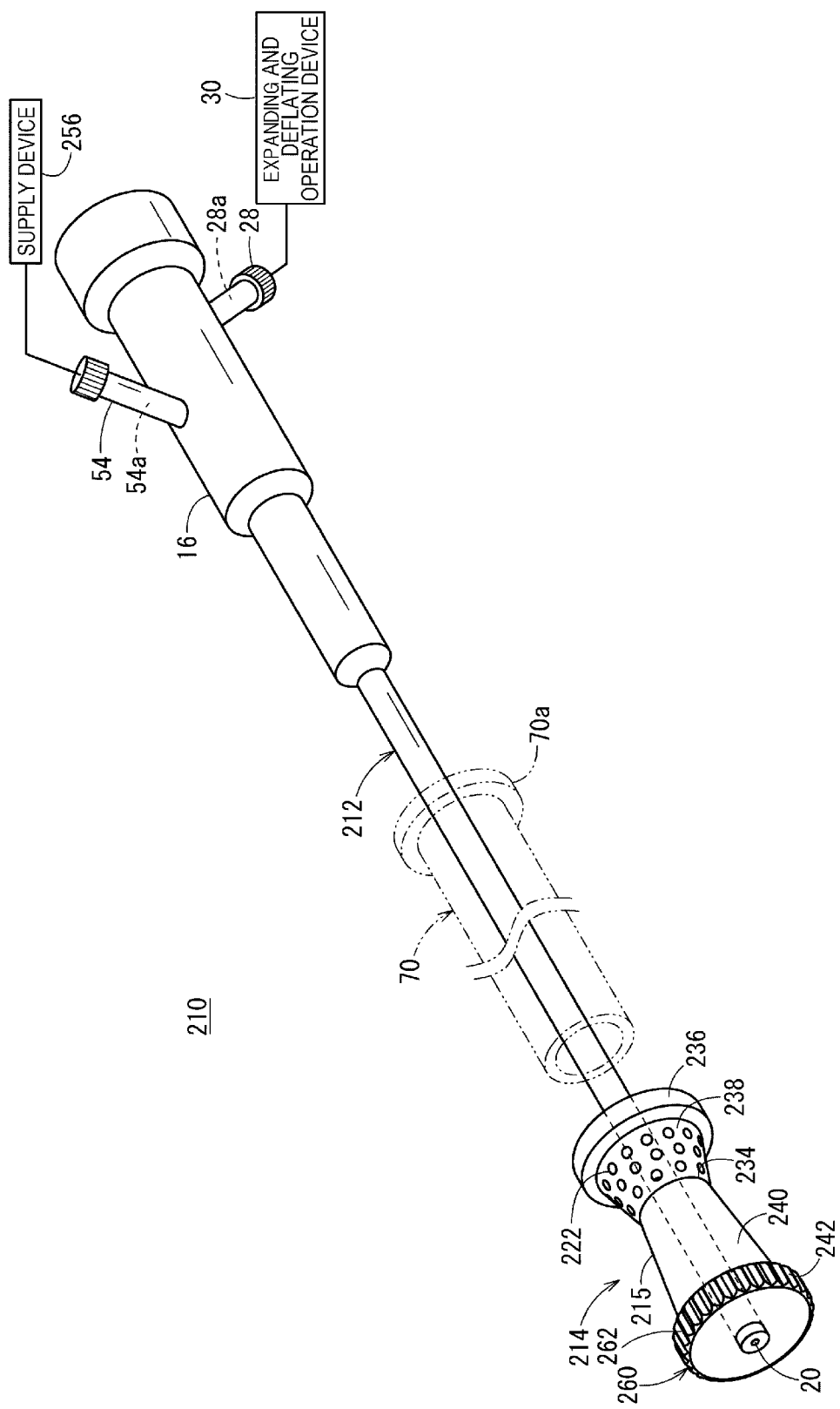
FIG. 9 is a perspective view showing an overall configuration of a device for treating the lumen of a living body according to a second embodiment of the present invention.

A balloon 14C according to a third modification example shown in FIGS. 8A to 8C is configured such that a plurality of coating portions 120 (5 portions in FIG. 8A) are provided between the proximal end protruding portion 36 and the distal end protruding portion 42 along the axial direction. The coating portions 120 have a proximal end inclination portion 122 (inclination portion on a discharge port side) and a distal end inclination portion 124 (inclination portion on a suction port side) within a short range in the axial direction. In this case, the proximal end inclination portion 122 includes the discharge port 22 and the distal end inclination portion 124 includes the suction port 24. Accordingly, the balloon 14C is configured so as to discharge and aspirate the pre-gel solution P through a single coating portion 120 and the plurality of coating portions 120 perform the same operation. Therefore, it is possible to favorably coat the coating chamber X with the pre-gel solution P.

Moreover, the balloon 14C can coat the pre-gel solution P such that small chevron shapes are connected along the axial direction of the blood vessel 80 as shown in FIG. 8B in accordance with the shape of the coating portion 120 arranged in the axial direction. After the coating of the pre-gel solution P, it is possible to reliably protect the treatment subject A, as shown in FIG. 8C. Moreover, the coating layer C in which the small chevrons are arranged forms a flatter coating layer C' which is made more smooth by being affected by the blood flow. Accordingly, it is possible to relatively evenly cover the treatment subject A in the blood vessel 80 and to favorably treat the treatment subject A. In particular, in a case of a pre-gel solution having a high viscosity, it is rather easy to guide the coating layer C after coating to a desired shape by forming such a coating layer C with small chevrons.

Next, a device 210 for treating the lumen of a living body (treatment device 210) according to a second embodiment will be described with reference to FIGS. 9 to 13C. Similar to the treatment device 10, the treatment device 210 includes a shaft 212, a balloon 214 (expansion and deflation body), and a hub 16. The shaft 212 has a guide wire lumen 20 into which a guide wire 18 is inserted.

The balloon 214 freely shifts between a deflated state in which an outer circumferential surface (recessed portion 244) is adjacent to (closer toward) the shaft 212 as shown in FIG. 10A and an expanded state in which the outer circumferential surface (recessed portion 244) is separated away from (farther from) the shaft 212 as shown in FIG. 10B. In addition, the discharge port 222 that ejects the pre-gel solution is provided at a predetermined position in the balloon 214. That is, the treatment device 210 functions to expand (inflate) and contract (deflate) the balloon 214 in the blood vessels and functions to discharge the pre-gel solution from the balloon 214.

The function of expanding and deflating the balloon 214 is realized using a first lumen 226 of the shaft 212, the balloon 214 itself, a first port 28 of the hub 16, and the expanding and deflating operation device 30 which is connected to the first port 28, as shown in FIGS. 9 and 11A to 11C. For more easily understanding the drawing, in FIG. 11A, the first lumen 226, the second lumen 250, the discharge guide path 251, and a communication port 250a are illustrated with simple lines for showing the route of a fluid. More specifically, the route of the fluid for expansion is shown by a solid line, and the flow path of the pre-gel solution is shown by a one-dot chain line. In addition, FIG. 11A is illustrated with a perspective view in order that an inner path 252b of the discharge guide path 252 of a protruding portion is more easily understood to have an annular shape.

The first lumen 226 of the shaft 212 is configured as a lumen for expansion fluid for supplying the fluid for expansion to the balloon 214 or for discharging the fluid for expansion from the balloon 214. The first lumen 226 is formed in a fan-shaped section that surrounds substantially one half of the portion outside of the guide wire lumen 20. For example, in FIG. 11B, the first lumen 226 is provided at the lower side of the guide wire lumen 20. The first lumen 226 extends along the axial direction of the shaft 212 and the proximal side of the first lumen communicates with a flow path 28a which is formed inside of the first port 28 within the hub 16.

The distal side of the first lumen 226 is bent or angled outwardly in a radial direction of the shaft 212 at a position axially overlapping with the balloon 214 and communicates with an internal space 232 of the balloon 214 through a side surface opening 226a of the shaft 212. The balloon 214 dilates outwardly in the radial direction of the shaft 212 by the fluid for expansion which is supplied to the internal space 232 and becomes the shape as shown in FIGS. 10B and 11A to 11C in the expanded state.

Specifically, the balloon 214 has a tubular shape having a constricted portion (constricted portion 234) and has a proximal end protruding portion 236 (first protruding portion), a proximal end inclination portion 238 (first inclination portion), a distal end inclination portion 240 (second inclination portion), and a distal end protruding portion 242 (second protruding portion).

A proximal end protruding end portion 236a and a distal end protruding end portion 242a which are protruded portions are provided outwardly in a radial direction of the proximal end protruding portion 236 and the distal end protruding portion 242. The side circumferential surfaces of the proximal end protruding end portion 236a and the distal end protruding end portion 242a come into contact with the inner surface of the blood vessels by protruding in a direction orthogonal to the axial direction of the shaft 212 in the expanded state.

The proximal end inclination portion 238 has a proximal end connecting end portion 238a which is of a size smaller than the proximal end protruding portion 236 and is connected to the proximal end protruding end portion 236a. Accordingly, a distal end surface 236b (facing surface) that faces the distal end direction is formed between the side circumferential surface of the proximal end protruding end portion 236a and the proximal end connecting end portion 238a. The proximal end inclination portion 238 shows a tapered shape gradually becoming smaller in diameter from the proximal end connecting end portion 238a toward the distal end direction and the distal end of the proximal end inclination portion is connected to the proximal end of the distal end inclination portion 240.

The distal end inclination portion 240 shows a tapered shape gradually becoming larger in outer diameter from the distal end of the proximal end inclination portion 238 toward the distal end direction. That is, the connection portion of the proximal end inclination portion 238 and the distal end inclination portion 240 in the balloon 214 is the constricted portion 234. The distal end inclination portion 240 is configured such that the length of the distal end inclination portion 240 along the axial direction of the balloon 214 is longer (greater) than the length of the proximal end inclination portion 238 in the axial direction of the balloon 214. Accordingly, the inclination angle of the distal end inclination portion 240 in the axial direction of the balloon 214 is gentler than that of the proximal end inclination portion 238.

The distal end inclination portion 240 has a distal end connecting end portion 240a which is of a size smaller than the distal end protruding portion 242 and is connected to the distal end protruding end portion 242a. Accordingly, a proximal end surface 242b that faces the proximal end direction is formed between the side circumferential surface of the distal end protruding end portion 242a and the distal end connecting end portion 240a.

In addition, similar to the balloon 14, the balloon 214 is configured to have a double structure including an inner balloon 214a and an outer balloon 214b. The balloon has a flow path for the pre-gel solution between the inner balloon 214a and the outer balloon 214b. The inner balloon 214a has an internal space 232 therein and shows a shape formed of the above-described proximal end protruding portion 236, proximal end inclination portion 238, distal end inclination portion 240, and distal end protruding portion 242 when the fluid for expansion is supplied to the internal space. The internal space 232 is provided with an annular-shaped gap 232a between the proximal end protruding portion 236 and the proximal end inclination portion 238 and between the distal end inclination portion 240 and the distal end protruding portion 242, to thereby ease the folding of the balloon 214. The outer balloon 214b deforms following the expansion and the deflation of the inner balloon 214a by covering the inner balloon 214a.

The balloon 214 (outer balloon 214b) is dilated so as to have the recessed portion 244 which is configured to have a distal end surface 236b of the proximal end protruding portion 236, an outer circumferential surface 238b of the proximal end inclination portion 238, an outer circumferential surface 240b of the distal end inclination portion 240, and the proximal end surface 242b of the distal end protruding portion 242. Then, in the expanded state, the balloon 214 forms a coating chamber X (refer to FIG. 12A or the like) between the recessed portion 244 and the inner surface of the blood vessels by bringing the proximal end protruding portion 236 and the distal end protruding portion 242 into contact with the inner surface of the blood vessels. A coating film 215 that reduces the adhesion of the pre-gel solution is provided on the surface of the balloon 214 (recessed portion 244).

Next, a function of discharging the pre-gel solution will be described with reference to FIGS. 9 and 11A to 11C. The function of discharging the pre-gel solution is realized using a second lumen 250 of the shaft 212, a discharge guide path 251 and a discharge port 222 of the balloon 214, a second port 54 of the hub 16, and a supply device 56 which is connected to the second port 54.

The second lumen 250 of the shaft 212 is a flow path (lumen for discharging) for supplying the pre-gel solution to the balloon 214. The second lumen 250 is a fan-shaped section that surrounds substantially one-half of the portion outside of the guide wire lumen 220. For example, in FIG. 11B, the second lumen 250 surrounds the upper half portion of the guide wire lumen 20. The second lumen 250 extends along the axial direction of the shaft 212 and the proximal side of the second lumen communicates with a flow path 54a which is formed inside of the second port 54 within the hub 16.

The cross section of the flow path of the second lumen 250 is the same as that of the first lumen 226, but the size of the second lumen 250 may be configured in accordance with the viscosity of the coating substance. In addition, it is preferable that the super-water-repellent coating film 258 or a riblet structure be formed inside of the second lumen 250 as means for reducing flow resistance in order to reduce the flow resistance (discharge resistance) of a pre-gel solution having a high viscosity.

The distal side of the second lumen 250 is bent or angled outwardly in a radial direction of the shaft 212 at a position overlapped with the proximal end protruding portion 236 of the balloon 214 and communicates with the communication ports 250a connected to the discharge guide path 251 which is formed in the proximal end protruding portion 236.

The discharge guide path 251 is formed of a space provided between the inner balloon 214a and the outer balloon 214b. The space may be formed by providing a groove which is manufactured on the outer circumferential surface of the inner balloon 214a or the inner surface of the outer balloon 214b, or a tube. The discharge guide path 251 is formed of a discharge guide path 252 of a protruding portion which is provided in the proximal end protruding portion 236 and a discharge guide path 253 of an inclination portion which are provided in the proximal end inclination portion 238.

The discharge guide path 252 of a protruding portion has a function of guiding the pre-gel solution outwardly in a radial direction from the communication ports 250a of the inside thereof. For example, the discharge guide path 252 of a protruding portion includes an introduction path 252a which communicates with the communication ports 250a, an inner path 252b circulating at a position close to the shaft 212, a plurality of intermediate paths 252c extending outwardly in a radial direction from the inner path 252b, and an outer path 252d which communicates with the intermediate paths 252c and circulates around the proximal end protruding end portion 236a.

The outer path 252d is connected to a connection path 252e extending to the proximal end protruding end portion 236a which is formed to be thick, in the thickness direction (axial or axis direction of the balloon 214). A plurality of connection paths 252e (12 paths in FIG. 11B) are provided along the circumferential direction of the outer path 252d and the distal portion communicates with the discharge guide path 253 of an inclination portion. The connection paths 252e are separated away from each other at even intervals.

A plurality of discharge guide paths 253 of an inclination portion is configured as a plurality of flow paths in accordance with the connection path 252e. The discharge guide paths 253 of an inclination portion linearly extend along the inside of the proximal end inclination portion 238 from the proximal end connecting end portion 238a to the vicinity of the constricted portion 234 and communicate with three discharge ports 222 along the axial direction of the balloon 214.

Figure 12A:
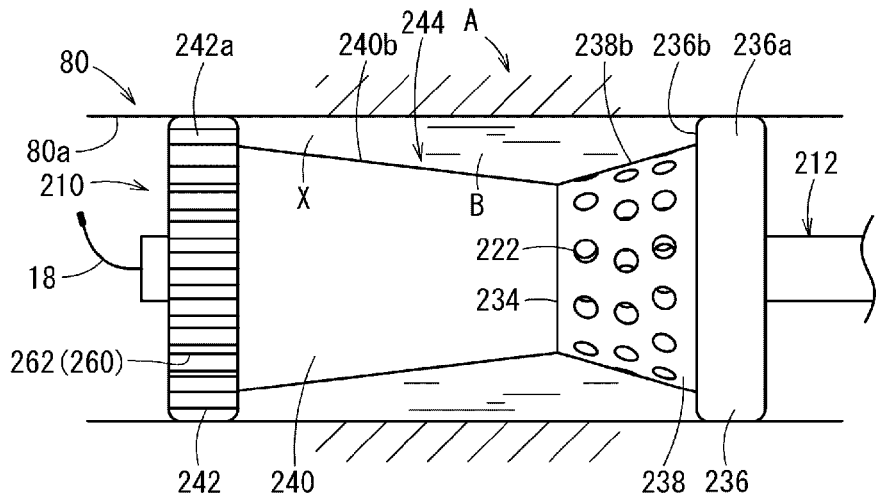
FIG. 12A is a first explanatory view describing a method of using the treatment device of FIG. 9.

A plurality of discharge ports 222 (12 ports) are provided in the circumferential direction of the proximal end inclination portion 238 and a plurality of rows (three (3) rows in FIG. 12A) of the discharge ports are formed in the axial direction of the proximal end inclination portion 238. The number of discharge guide paths 253 of an inclination portion is set in accordance with the number of discharge ports 222 (12 ports) formed in the circumferential direction. The discharge ports 222 substantially evenly discharge the pre-gel solution, which is guided to the discharge guide paths 253 of an inclination portion, to the outside (recessed portion 244) of the balloon 214.

Returning to FIG. 9, the supply of the pre-gel solution is operated using the supply device 256 which is connected to the second port 54 of the hub 16. In addition, it is preferable that the supply device 256 include a pressure detection unit that monitors the discharge pressure (delivery pressure) of the pre-gel solution. Accordingly, the operator can recognize the fluctuation of the discharge pressure of the pre-gel solution.

Furthermore, as shown in FIGS. 10B, 11A, and 11C, the distal end protruding portion 242 of the balloon 214 is provided with discharge means 260 for discharging a substance existing in the coating chamber X to the outside of the balloon 214. The discharge means 260 is formed of groove portions 262 (communication paths) which are provided on an outer circumferential surface of the distal end protruding end portion 242a (outer balloon 214b).

The groove portions 262 have a predetermined depth inward in a radial direction from the outer circumferential surface of the distal end protruding end portion 242a and linearly extend along the thickness direction (axial direction of the balloon 214) of the distal end protruding end portion 242a which is formed to be thick. A plurality of groove portions 262 are formed at even intervals along the circumferential direction of the distal end protruding end portion 242a. Accordingly, the outer circumferential surface of the distal end protruding end portion 242a is formed in a concave-convex shape by the groove portions 262 and a partition wall 264 formed between the adjacent groove portions 262.

In the expanded state of the balloon 214 in the blood vessels, the partition wall 264 comes into contact with the inner surface of the blood vessels and the groove portion 262 is disposed at a non-contact position relative to the inner surface of the blood vessels. For this reason, the recessed portion 244 (coating chamber X) inside of the balloon 214 communicates with the outside (distal side) of the balloon 214. The groove portion 262 reduces the amount of the pre-gel solution having a high viscosity that is discharged outside the balloon 214 while enabling blood or a saline solution, to be described later, in the coating chamber X to flow outside the balloon 214. In addition, it is possible to control the flow of the pre-gel solution in the coating chamber X by discharging the liquid in the coating chamber X from the groove portion 262.

The treatment device 210 according to the second embodiment is configured as described above. Next, operational aspects and the effect of the treatment device 210 will be described with reference to FIGS. 12A to 13C.

Similar to the treatment device 10, in the treatment device 210 the delivery step and the expansion step are operated by the operator. Moreover, a step of forming a coating environment is carried out in order to discharge the blood B left in the recessed portion 244 of the balloon 214.

Figure 12B:
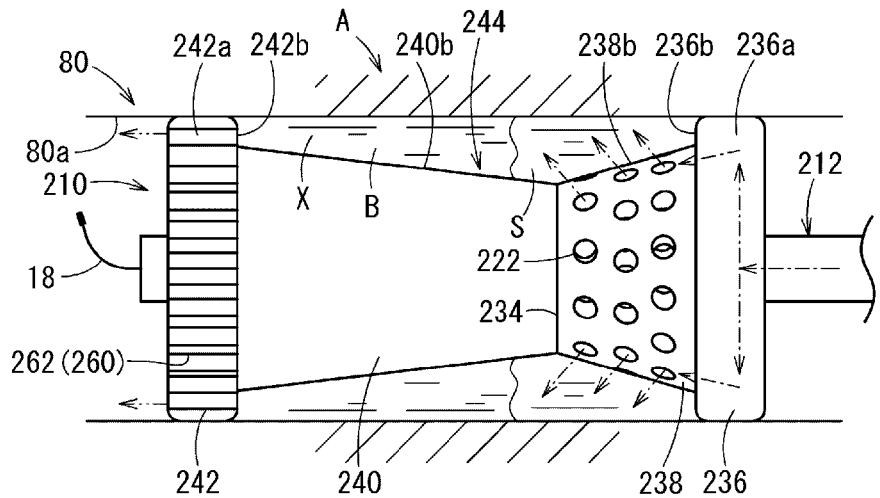
FIG. 12B is a second explanatory view describing the method of using the same subsequent to FIG. 12A.

More specifically, a saline solution S is discharged from the discharge port(s) 222 of the balloon 214. The saline solution S flows into the discharge guide path 251 of the balloon 214 through the flow path 54a of the second port 54 and the second lumen 250 (refer to FIG. 11A) of the shaft 212 using the supply device 256 (refer to FIG. 9). Then, the saline solution S flows through the discharge guide path 251 to be discharged to the inside of the coating chamber X from the discharge port 222. As shown in FIG. 12B, the saline solution S which is discharged to the coating chamber X flows toward the distal end direction by sweeping away the blood B existing in the coating chamber X.

The distal end protruding portion 242 of the balloon 214 is provided with the groove portion 262 (discharge means 260) as described above. For this reason, once the saline solution S is discharged from the discharge port 222, the blood B in the coating chamber X is swept away toward the distal end direction in the coating chamber X. As a result, the blood B is pushed in the distal end direction and is discharged to the outside of the recessed portion 244 (balloon 214) through the groove portion 262. At this time, the balloon 214 has the discharge means 260 on a surface facing the discharge port 222. Therefore, it is possible to efficiently fill the inside of the coating chamber X with the saline solution S (or pre-gel solution P).

Figure 12C:
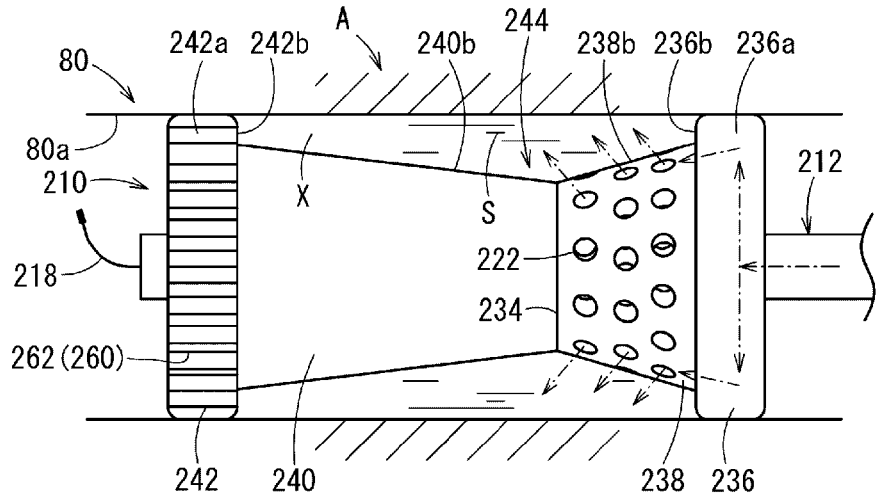
FIG. 12C is a third explanatory view describing the method of using the same subsequent to FIG. 12B.

The coating environment in which the coating chamber X is filled with the saline solution S is formed as shown in FIG. 12C. The treatment device 210 sweeps away the blood B to the outside of the coating chamber X in accordance with the amount of the saline solution S discharged from the discharge port 222. Thus, it is possible to form the coating environment without greatly changing the pressure exerted on the inside of the coating chamber X. As a matter of course, the step of forming a coating environment may not be carried out depending on the treatment situation.

Figure 13A:
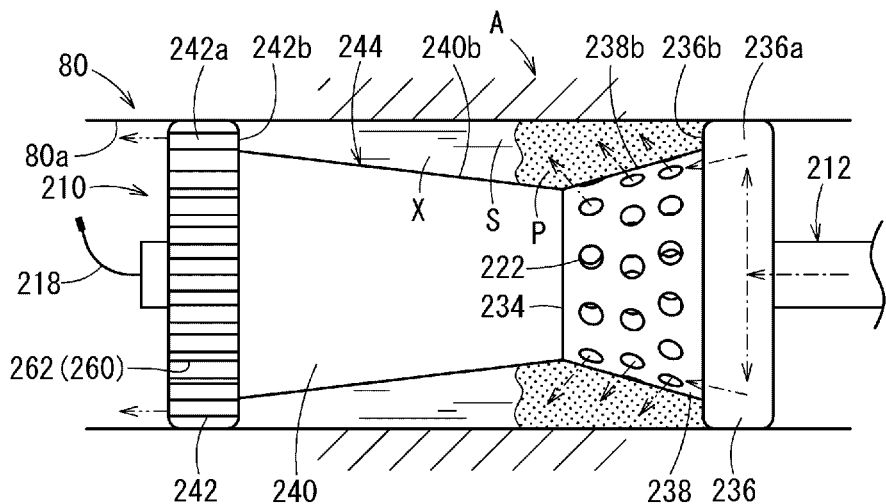
FIG. 13A is a fourth explanatory view describing the method of using the same subsequent to FIG. 12C.

After the inside of the coating chamber X is filled with the saline solution S, the pre-gel solution P is discharged to the inside of the coating chamber X (coating step). The pre-gel solution P flows into the discharge guide path 252 of a protruding portion of the discharge guide path 251 of the balloon 214 from the communication ports 250a of the second lumen 250. The pre-gel solution P flows into the introduction path 252a, is diffused in the circumferential direction by passing through the inner path 252b, and flows into the plurality of intermediate paths 252c. Furthermore, the diffusion is promoted by the pre-gel solution P flowing into the outer path 252d from the intermediate paths 252c. The pre-gel solution P guided to the outer path 252d is further guided to the discharge guide path 253 of an inclination portion through the connection path 252e to move in the discharge guide path 253 of an inclination portion. Then, as shown in FIG. 13A, the pre-gel solution P is discharged from the discharge port 222 arranged in the axial direction. Accordingly, a large quantity of pre-gel solution P flows to the distal side of the coating chamber X from the outer circumferential surface 238b of the proximal end inclination portion 238. The discharge port)s) 222 is in the proximal end inclination portion 238, and therefore, the distance between the blood vessel wall and the discharge port is rather short. Thus, it is possible to efficiently coat the blood vessel wall with the pre-gel solution P.

Figure 13B:
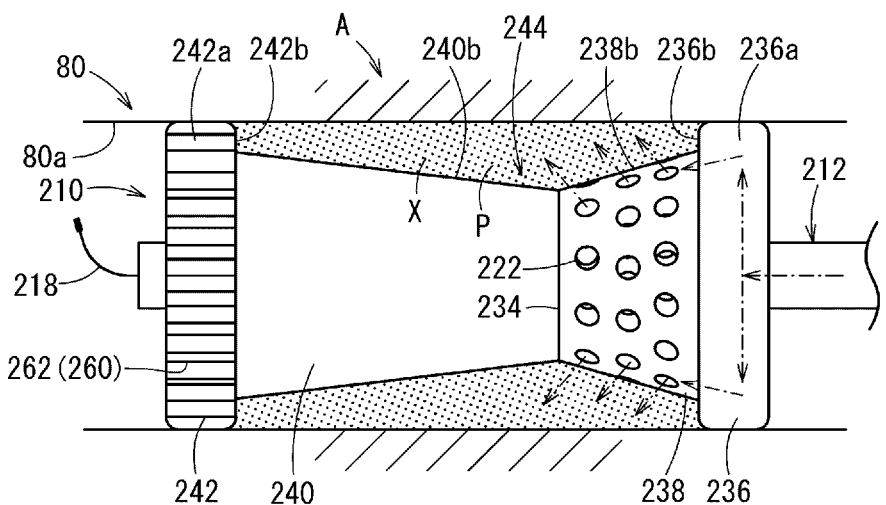
FIG. 13B is a fifth explanatory view describing the method of using the same subsequent to FIG. 13A.

In addition, when discharging the pre-gel solution P, the saline solution S is discharged from the groove portion 262 (discharge means 260), and therefore, the saline solution S and the pre-gel solution P in the coating chamber X smoothly flow in the distal end direction from the discharge port 222. As a result, as shown in FIG. 13B, the coating chamber X rather easily enters a state of being filled with the pre-gel solution P from a state of being filled with the saline solution S. The pre-gel solution P in the filled state in the coating chamber X exists in a shape corresponding to the coating chamber X, that is, an annular shape. The groove portion 262 suppresses or blocks the pre-gel solution P having a high viscosity from being discharged while the groove portion 262 allows the saline solution S to be discharged. Therefore, it is possible to reliably fill the inside of the coating chamber X with the pre-gel solution P.

Here, the pressure detection unit of the supply device 256 (refer to FIG. 9) monitors the discharge pressure of the pre-gel solution P. Moreover, once the coating chamber X is filled with the pre-gel solution P, the pressure detection unit detects that the discharge pressure steeply increases because of the pre-gel solution P not being discharged from the recessed portion 244. Accordingly, the operator can simply recognize that the coating chamber X is filled with the pre-gel solution P by monitoring the discharge pressure. Once the pre-gel solution P is filled therein, the operation of the supply device 256 stops and the discharge operation stops.

Figure 13C:
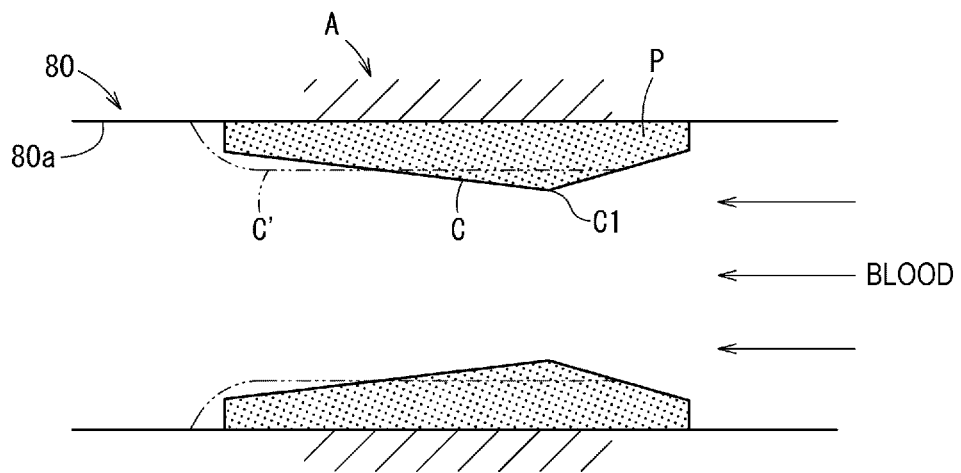
FIG. 13C is a sixth explanatory view describing the method of using the same subsequent to FIG. 13B.

After coating the pre-gel solution P, an operation of deflating the balloon 214, and an operation of removing the treatment device 210 from the blood vessel 80 are performed. Accordingly, the gel-like coating layer C is implanted in the blood vessel 80 in a chevron cross section shape as shown in FIG. 13C.

The gel-like coating layer C, the viscosity of which is higher than viscosity during discharging, is formed on the inner surface 80a of the blood vessel 80 along the shape of the recessed portion 244 of the balloon 214. Here, the portion (portion coming into contact with blood) separated from the blood vessel wall of the coating layer C is rather easily affected by the shear stress due to the blood flow since the flow velocity of the blood flow is high compared to that of the blood vessel wall. For this reason, in some cases, the shape of the coating layer C is deformed by the blood flow in the blood vessel 80 before the gelation, and thus, it is impossible to appropriately protect the treatment subject A. For this reason, the treatment device 210 forms the coating layer C in consideration of the blood flow.

The balloon 214 of the treatment device 210 forms the coating layer C so as to make the top portion C1 of the chevron lean further in the upstream direction of the blood flow than the central portion in the axial direction of the coating layer C. For this reason, once blood restarts flowing through the inside of the blood vessel 80 after the deflating of the treatment device 210, the area around the top portion C1 of the chevron of the coating layer C moves in the downstream direction by being affected by the flow of blood. That is, the coating layer C is changed to have an appropriate coating shape and to be within an appropriate range for coating so as to be made smooth as shown by the two-dot chain line in FIG. 13C by the shear stress of the blood flow, thereby covering the treatment subject A. Accordingly, it is possible to favorably protect or treat the treatment subject A.

As described above, according to the treatment device 210 according to the second embodiment, it is possible to smoothly fill the inside of the recessed portion 244 of the balloon 214 with the pre-gel solution P by discharging the pre-gel solution P from the plurality of discharge ports 222 provided in the proximal end inclination portion 238. Furthermore, the constricted portion 234 is positioned deviated from the central portion in the axial direction (axial center)

of the recessed portion 244, and thus, the recessed portion 244 forms the coating layer C, of which the top portion C1 of the chevron is deviated, of the pre-gel solution P. For this reason, the coating layer C is made smooth by the blood flow and is changed to have an appropriate coating shape by coating the pre-gel solution such that the top portion C1 of the chevron is deviated to the upstream side of blood flowing through the inside of the blood vessel 80. Accordingly, it is possible to favorably protect or treat the treatment subject A of the blood vessel 80. In addition, while treating the treatment subject A, it is possible to form the coating layer containing a biological substance which is physiologically active in the vicinity of the treatment subject A by mixing the pre-gel solution P with the biological substance which is physiologically active. Moreover, it is possible to apply the biological substance which is physiologically active to the treatment subject A in a controlled-release manner.

In addition, the treatment device 210 can discharge the blood B or the saline solution S within the coating chamber X through the groove portion 262 while discharging the pre-gel solution P toward the inside of the coating chamber X from the discharge port 222 by providing the groove portion 262 (discharge means 260). Accordingly, it is possible to simply fill the coating chamber X with the pre-gel solution P. The groove portion 262 can be simply provided, and therefore, it is possible to reduce the manufacturing cost or the like of the treatment device 210.

Various modifications and application examples can also be made in the treatment device 210 according to the second embodiment. Hereinafter, several modification examples of the treatment device 210 will be described.

Figure 14:
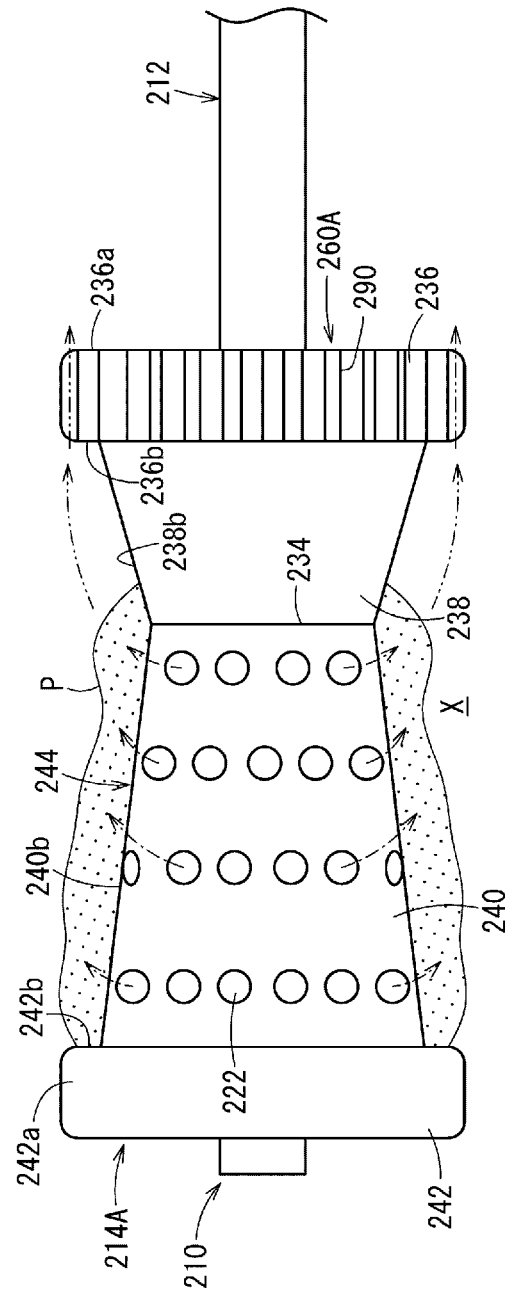
FIG. 14 is a side view showing a distal portion of a treatment device according to a fourth modification example.

A balloon 214A according to a fourth modification example shown in FIG. 14 is configured such that a plurality of discharge ports 222 are provided on the outer circumferential surface 260b of the distal end inclination portion 240 and a groove portion 290 as discharge means 260A is provided in the proximal end protruding portion 236. Even with such a configuration, the pre-gel solution P or the saline solution S discharged from the discharge port 222 can smoothly flow in the recessed portion 244 (coating chamber X) in the proximal end direction. For this reason, it is possible to form the coating layer C of the pre-gel solution P to be the same as that of the balloon 214. In particular, in a case where the distal side of the balloon 214A is in the upstream side of the blood flow, it is possible to preferably use the balloon 214A.

Furthermore, in discharge means 260B (balloon 214B according to a fifth modification example), in order to make the pre-gel solution P hardly flow, for example, a recessed groove portion 292 may be provided with an opening and closing mechanism 294 (openable plate-like object) such as a curtain as shown in FIG. 15A. Accordingly, the opening and closing mechanism 294 of the groove portion 292 enters an opened state when the pressure within the coating chamber X exceeds a constant value. Therefore, it is possible to discharge the liquid in the coating chamber X to the outside of the coating chamber X. For this reason, it is possible to control the pressure within the coating chamber X so as not to be greater than a constant value.

In addition, as shown in FIG. 15B, discharge means 260C (balloon 214C according to a sixth modification example) may be formed to provide the groove portion 292 with a porous body structure 296 (as an obstruction) such as a sponge. The porous body structure 296 allows a liquid having a relatively low viscosity flow easily and a solution having a relatively high viscosity hardly flow at all.

Furthermore, as shown in FIG. 15C, discharge means 260D (balloon 214D according to a seventh modification example) may be configured as a penetration path 298. In this case, it is preferable that the penetration path 298 be formed to be tapered (such as a check valve) so as to easily cause pressure loss.

In short, the discharge means 260 and 260A to 260D can employ various structures such as the communication path (groove portion) or the penetration path. In addition, in the discharge means such as the communication path or the penetration path, the discharge condition or the discharge amount of a fluid within the coating chamber X using the discharge means can be adjusted by providing an opening and closing structure, an obstruction, a tapered structure, or the like. A structure (suction port) of aspirating a fluid within the coating chamber X may be provided as the discharge means. In addition, the formation positions, the number of formations, the shape or the like of the discharge ports 222 formed in the balloon 214 are not particularly limited and can be freely set.

Figure 16A:
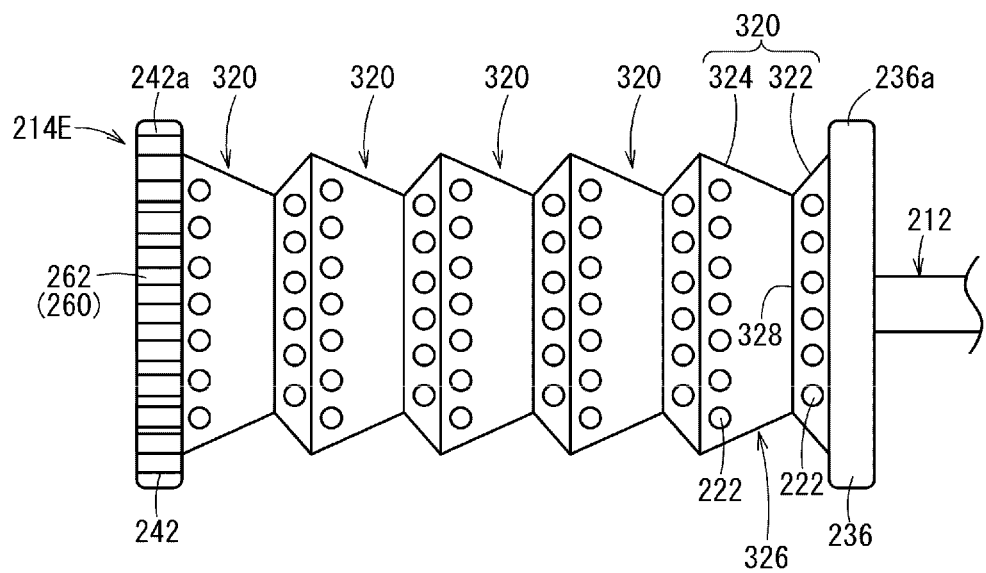
FIG. 16A is a side view showing a distal portion of a treatment device according to an eighth modification example.
Figure 16B:
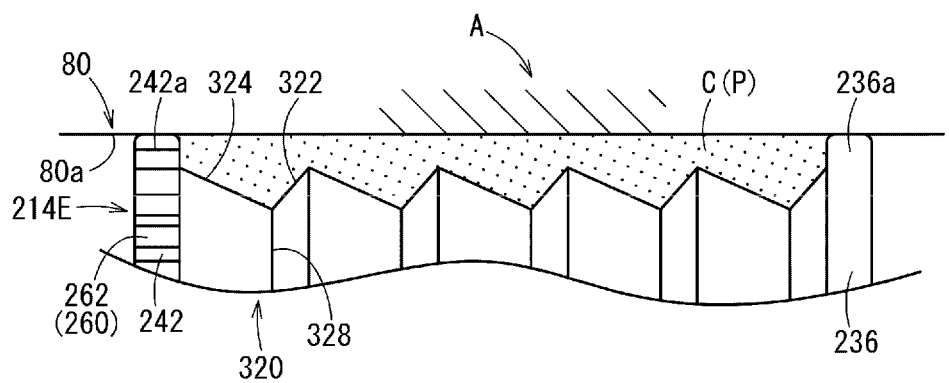
FIG. 16B is a partial side view showing a coating state of a coating substance of the treatment device of FIG. 16A.
Figure 16C:
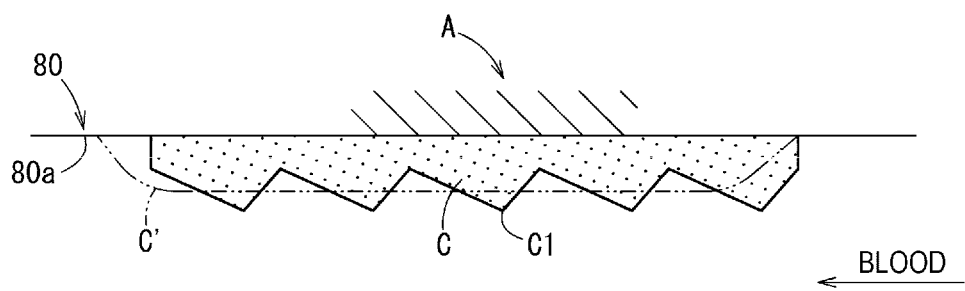
FIG. 16C is a partial side view showing a state of the coating substance after being coated subsequent to FIG. 16B.

Similar to the balloon 14C according to the third modification example, a balloon 214E according to an eighth modification example shown in FIGS. 16A to 16C has a plurality of coating portions 320 along the axial direction between the proximal end protruding portion 236 and the distal end protruding portion 42. The coating portion 320 respectively constitutes recessed portions 326 with the outer circumferential surfaces of the proximal end inclination portion 322 and the distal end inclination portion 324. The circumferential surfaces of the proximal end inclination portion 322 and the distal end inclination portion 324 are provided with the discharge port(s) 222. In addition, a constricted portion 328 (connection portion) of the proximal end inclination portion 322 and the distal end inclination portion 324 are deviated in the proximal end direction from the central portion in the axial direction (axial center) of the recessed portion 326.

Groove portion (openings or spaces) 262 as the discharge means 260 is formed in the distal end protruding portion 242 of the balloon 214E. Accordingly, the balloon 214E discharges a fluid within the coating chamber X to the outside through the groove portion 262 while discharging a large quantity of the pre-gel solution P to the coating chamber X configured to have a plurality of recessed portions 326.

Similar to the balloon 14C, the balloon 214E coats the pre-gel solution P such that small chevron shapes are connected along the axial direction of the blood vessel 80 (refer to FIG. 16B). After the coating, the coating layer C is affected by the blood flow and forms a flatter coating layer C′ which is made smoother (refer to FIG. 16C). In addition, in a case of the balloon 214E provided with a plurality of recessed portions 326, it is possible to efficiently fill the inside of the coating chamber X with the pre-gel solution P by providing both of the proximal end inclination portion 322 and the distal end inclination portion 324 with the discharge port 222.

In addition, as common modification examples of the treatment device 10 according to the first embodiment and the treatment device 210 according to the second embodiment, for example, it is possible to employ the shapes shown in FIGS. 17A to 17D. In a balloon 414A according to a ninth modification example shown in FIG. 17A, the shapes of a plurality of coating portions 430 are changed stepwise along the axial direction of the balloon 414A. That is, in the expanded state of the balloon 414A, the coating portions 430 on the proximal side dilate inward in a radial direction and the expansion amount of the coating portions 430 increases stepwise outwardly in a radial direction toward the distal end direction from the proximal side. In this case, a configuration (suction port or discharge means) for discharging blood B (or saline solution S) from the recessed portion 420 of the coating portion 430 can be set to be the same as that of the third modification example or the eighth modification example.

The pre-gel solution P is coated in the blood vessel 80 so as to gradually decrease toward the downstream side from the upstream side of the blood flow (proximal portion of the balloon 414A) using the balloon 414A. In this manner, once the pre-gel solution P is coated, the pre-gel solution P, on an upstream side, which is significantly affected by the blood flow after the coating, easily moves to the downstream side. Accordingly, it is possible to favorably treat the treatment subject A using the pre-gel solution P by simply being made smooth so as to have a desired shape.

Figure 17A:
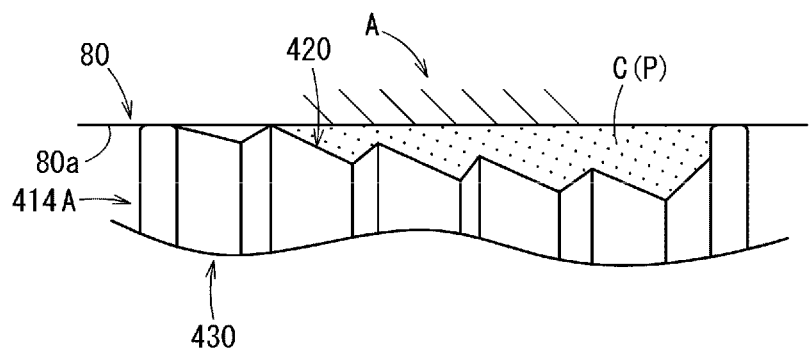
FIG. 17A is a partial side view showing a coating state of a coating substance of a treatment device according to a ninth modification example.
Figure 17B:
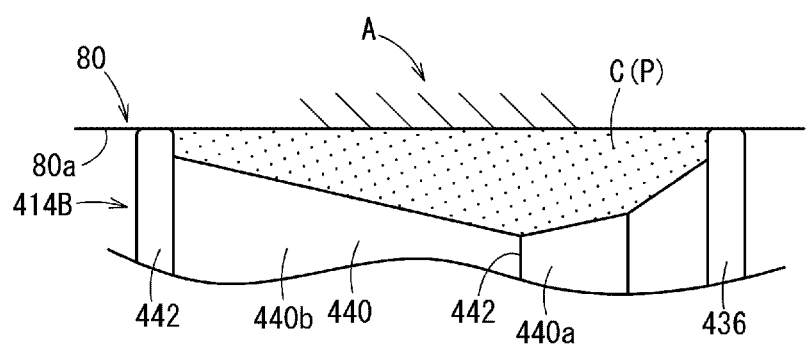
FIG. 17B is a partial side view showing a coating state of a coating substance of a treatment device according to a tenth modification example.

A balloon 414B according to a tenth modification example shown in FIG. 17B is configured to have three or more outer circumferential surfaces 440 (three surfaces in FIG. 17B) between the proximal end protruding portion 436 and the distal end protruding portion 442. In this case, a constricted portion 442 is set between a first inclination portion 440a and a second inclination portion 440b by setting the second inclination portion 440b in a portion connected to the distal end protruding portion 442 and setting the first inclination portion 440a in a portion connected to the second inclination portion 440b, for example. Accordingly, the coating layer C of the pre-gel solution P is also formed in a polyhedral shape following the outer circumferential surface 440 of the balloon 414B. In this manner, it is possible to form the coating layer C having a more even height even in a case where the length of the coating layer C of the pre-gel solution P is longer, using the coating layer C formed in a more polyhedral shape.

Figure 17C:
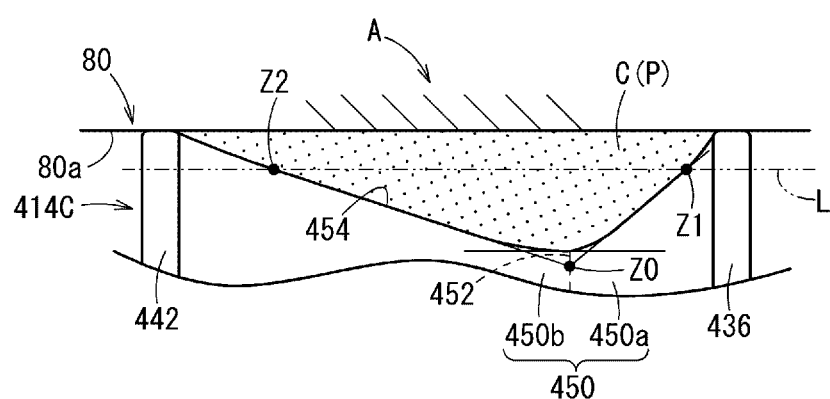
FIG. 17C is a partial side view showing a coating state of a coating substance of a treatment device according to an eleventh modification example.

A balloon 414C according to an eleventh modification example shown in FIG. 17C is configured such that an outer circumferential surface 450 between the proximal end protruding portion 436 and the distal end protruding portion 442 has a smoothly curved surface. That is, the "first inclination portion" and the "second inclination portion" of the balloon in the present specification are not limited to being formed in a linear outer circumferential surface in side view and include a curved outer circumferential surface. In a case where the outer circumferential surface 450 of the balloon 414C has a curved surface (curved line), a constricted portion 452 (connection portion) of a first inclination portion 450a and a second inclination portion 450b corresponds to a portion where the outer diameter becomes minimum. Accordingly, the coating layer C of the pre-gel solution P is also formed in a smoothly curved surface shape along the outer circumferential surface 450 of the balloon 414C. In this manner, it is possible to make the top portion hardly flow due to the blood flow by making the shape of the coating layer C of the pre-gel solution P be the curved surface shape.

In the case of the configuration of FIG. 17C, for example, in the balloon 414C, the first inclination portion 450a is a portion connected to the distal end protruding portion 442 and the second inclination portion 450b is a portion connected to the proximal end protruding portion 436. In this case, the constricted portion 452 can be a portion where the inclination of a tangent when a tangent is drawn on the outer circumferential surface 450 between the first inclination portion 450a and the second inclination portion 450b becomes 0° relative to the axis of the shaft 12 (refer to FIG. 1). In FIG. 17C, when a virtual line L parallel to the axis of the shaft 12 is drawn so as to overlap with the outer circumferential surface 450, a first intersection Z1 between the curved surface and the virtual line L exists in the first inclination portion 450a and a second intersection Z2 exists in the second inclination portion 450b. At this time, an intersection Z0 of the tangent between the first intersection Z1 and the second intersection Z2 in the curved surface is set to be positioned deviated in the proximal end direction from the central portion in the axial direction of the recessed portion 454 of the balloon 414C.

Figure 17D:
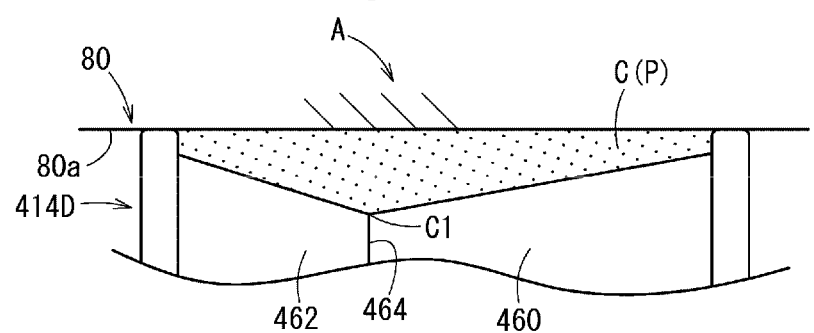
FIG. 17D is a partial side view showing a coating state of a coating substance of a treatment device according to a twelfth modification example.

A balloon 414D according to a twelfth modification example shown in FIG. 17D is configured such that the proximal end inclination portion 460 has a gentle inclination angle and the distal end inclination portion 462 has a steep inclination angle. For this reason, the constricted portion 464 of the balloon 414D is formed further on the distal side than the central portion in the axial direction of the balloon 414D. It is possible to form the coating layer C of the pre-gel solution P such that the top portion C1 is positioned on the distal side along the outer circumferential surface of the balloon 414D by making the position of the constricted portion 464 lean to the distal side in this manner.

In short, the shapes of the balloons 14 and 214 of the treatment devices 10 and 210 are not particularly limited and may be appropriately designed. Moreover, the discharge port 22 and 222 and the suction port 24 (or discharge means 260) may be provided at appropriate places such that the coating chamber X can be favorably filled with the pre-gel solution P in accordance with the shapes of the balloons 14 and 214. In the balloons 14 and 214, the recessed portion is not only provided over the entire circumference of the outer circumferential surface, but may also be partially provided in the circumferential direction. Moreover, the other portion in the circumferential direction may be a protruding area that blocks the recessed portion.

In addition, as another modification example of the treatment devices 10 and 210, a procedure may be performed without blocking blood flow during the coating of the pre-gel solution. In this case, a space through which blood can pass may be formed in the balloons 14 and 214. Furthermore, the expansion and deflation bodies of the treatment devices 10 and 210 are not limited to the balloons 14 and 214 and various structures having a recessed portion that forms a coating chamber X within a lumen of a living body in the expanded state can be employed.

The detailed description above describes a lumen treating device for treating a lumen in a living body. The invention is not limited, however, to the precise embodiments and variations or modifications described. Various changes, modifications and equivalents can be implemented by one skilled in the art without departing from the spirit and scope of the invention as defined in the accompanying claims. It is expressly intended that all such changes, modifications and equivalents which fall within the scope of the claims are embraced by the claims.

What is claimed is:

1. A device for treating a lumen of a living body, comprising:
    a shaft configured to be inserted into the lumen of the living body, the shaft comprising a first lumen and a second lumen separate from one another;
    an expansion and deflation body provided on the shaft and changeable between a deflated state and an expanded state;
    wherein, in the expanded state, the expansion and deflation body includes:

at least one recessed portion configured to form a coating chamber which is substantially blocked between an inner surface of the lumen of the living body and the expansion and deflation body;

a discharge port which is connected to the first lumen and is provided on the recessed portion and which discharges a coating substance via the first lumen toward the coating chamber; and a suction port which is connected to the second lumen and is provided on the recessed portion and which aspirates fluid via the second lumen from the coating chamber.

2. The device for treating a lumen of a living body according to claim 1, wherein, in the expanded state, the expansion and deflation body is tubular-shaped and possesses two end portions at opposite axial ends of the body, one of the end portions of the body in the expanded state including an outwardly protruding first protruding portion, the other end portion of the body in the expanded state including an outwardly protruding second protruding portion, the body in the expanded state also including an intermediate portion possessing an outer surface, the first and second protruding portions protruding outwardly beyond the outer surface of the intermediate portion of the body in the expanded state.

3. The device for treating a lumen of a living body according to claim 2, wherein the discharge port opens to a surface of the second protruding portion that faces axially toward the first protruding portion, and wherein the suction port opens to a surface of the first protruding portion that faces axially toward the second protruding portion.

4. The device for treating a lumen of a living body according to claim 2, wherein the recessed portion includes a first inclination portion connected to the first protruding portion and extending towards the second protruding portion, and a second inclination portion connected to the second protruding portion and extending towards the first protruding portion, the first inclination portion being connected to the second inclination portion at a connection portion, the connection portion being most inwardly recessed of the recessed portion between the first protruding portion and the second protruding portion.

5. The device for treating a lumen of a living body according to claim 4, wherein, in the expanded state, the connection portion is disposed at a position axially deviated toward the first protruding portion from a center of the recessed portion.

6. The device for treating a lumen of a living body according to claim 4, wherein a plurality of the discharge ports are circumferentially spaced apart along the first inclination portion, and wherein a plurality of the suction ports are circumferentially spaced apart along the second inclination portion.

7. The device for treating a lumen of a living body according to claim 6, wherein the plurality of discharge ports are also spaced apart along the axial direction of the first inclination portion.

8. The device for treating a lumen of a living body according to claim 4, wherein the plurality of discharge ports are circumferentially spaced apart along the first inclination portion at a position near the connection portion of the first inclination portion and the second inclination portion, and wherein the plurality of suction ports are circumferentially spaced along the first inclination portion near the first protruding portion and are circumferentially spaced apart along the second inclination portion near the second protruding portion, the plurality of discharge ports being positioned axially between the suction ports near the first protruding portion and the suction ports near the second protruding portion.

9. The device for treating a lumen of a living body according to claim 1, wherein the expansion and deflation body has a plurality of axially spaced coating portions, each possessing an inclination portion on a discharge port side to which the discharge port is provided connected to an inclination portion on a suction port side to which the suction port is provided, the inclination portion on the discharge port side being axially arranged relative to the inclination portion on the suction port side.

10. The device according to claim 1, wherein the expansion and deflation body is one piece and is formed as a single unitary structure.

11. The device according to claim 1, further comprising a plurality of discharge ports and a plurality of suction portions, and wherein all of the discharge ports and all of the suction ports are spaced apart from an inner surface of the lumen of the living body.

12. A device for treating a lumen of a living body, comprising:

a shaft configured to be inserted into the lumen of the living body;

an expansion and deflation body provided on the shaft and changeable between a deflated state and an expanded state;

wherein, in the expanded state, the expansion and deflation body includes:

at least one axially extending recessed portion that includes a first inclination portion and a second inclination portion that are inclined in different directions and arranged axially adjacent one another to form a coating chamber between an inner surface of the lumen of the living body and the expansion and deflation body in the expanded state when the expansion and deflation body is positioned in the lumen and expanded to the expanded state;

a discharge port on the first inclination portion which discharges a coating substance toward the coating chamber; and wherein, in the expanded state, a connection portion of the recessed portion at which the first inclination portion and the second inclination portion are connected is disposed at a position axially deviated in a proximal end direction from a center of the recessed portion.

13. The device for treating a lumen of a living body according to claim 12, the expansion and deflation body is tubular-shaped and possesses two end portions at opposite axial ends of the body, one of the end portions of the body in the expanded state including an outwardly protruding first protruding portion, the other end portion of the body in the expanded state including an outwardly protruding second protruding portion, the body in the expanded state also including an intermediate portion possessing an outer surface, the first and second protruding portions protruding outwardly beyond the outer surface of the intermediate portion of the body in the expanded state, the first protruding portion and the second protruding portion being positioned adjacent to or in abutment with an inner surface of the lumen of the living body when the expansion and deflation body is positioned in the lumen in the living body and is expanded to the expanded state.

14. The device for treating a lumen of a living body according to claim 13, wherein the first protruding portion is at a proximal portion of the expansion and deflation body and includes an axially facing outer surface which faces the second protruding portion, the second protruding portion being at a distal portion of the expansion and deflation body and including an axially facing outer surface which faces the first protruding portion, the first inclination portion being directly connected to the axially facing outer surface of the first protruding portion, the second inclination portion being directly connected to the axially facing outer surface of the second protruding portion.

15. The device for treating a lumen of a living body according to claim 13, wherein the discharge port is provided on the first inclination portion, and wherein the second protruding portion includes a plurality of openings configured to discharge a fluid in the coating chamber out of the coating chamber.

16. The device for treating a lumen of a living body according to claim 15, wherein the plurality of openings configured to discharge the fluid in the coating chamber out of the coating chamber are located at the second protruding portion and are configured to define a communication path that communicates the coating chamber with outside of the expansion and deflation body.

17. The device for treating a lumen of a living body according to claim 12, wherein the expansion and deflation body includes an inner balloon that has an inner space communicating with a lumen passing through the shaft that conveys expansion fluid, and an outer balloon that covers the inner balloon, and wherein a flow path communicating with the discharge port is between the inner balloon and the outer balloon.

18. The device for treating a lumen of a living body according to claim 12, wherein the shaft includes a lumen for discharging which communicates with the discharge port, and further comprising means for reducing flow resistance that reduces the flow resistance of the coating substance in the lumen for discharging, the means for reducing flow resistance being provided on an inner surface of the lumen for discharging.

19. The device for treating a lumen of a living body according to claim 12, wherein means for reducing adhesion of the coating substance that reduces adhesion of the coating substance is provided on the surface of the expansion and deflation body.

20. A device for treating a lumen of a living body, comprising:
   a shaft configured to be inserted into the lumen of the living body;
   an expansion and deflation body provided on the shaft and changeable between a deflated state and an expanded state;
   wherein, in the expanded state, the expansion and deflation body includes:
      at least one recessed portion that is recessed relative to portions of the expansion and deflation body on opposite axial ends of the recessed portion and that is configured to form a coating chamber which is substantially blocked between an inner surface of the lumen of the living body and the expansion and deflation body;
      a discharge port which is provided on the recessed portion and which is configured to discharge into the coating chamber at different times both a fluid and a coating substance which are different from one another;
      a suction port which is provided on the recessed portion and which is configured to suction fluid from the coating chamber, and the suction portion being configured to suction fluid from the coating chamber while the discharge port discharges the fluid to the coating chamber.

\* \* \* \* \*